United States Patent
Yin et al.

(10) Patent No.: US 9,975,916 B2
(45) Date of Patent: May 22, 2018

(54) COMPOSITIONS AND METHODS RELATING TO COMPLEX NUCLEIC ACID NANOSTRUCTURES

(71) Applicant: President and Fellows of Harvard College, Cambridge, MA (US)

(72) Inventors: Peng Yin, Brookline, MA (US); Diming Wei, Cambridge, MA (US); Mingjie Dai, Boston, MA (US); Cameron Myhrvold, Cambridge, MA (US); Yonggang Ke, Atlanta, GA (US); Ralf Jungmann, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 199 days.

(21) Appl. No.: 14/440,907

(22) PCT Filed: Nov. 6, 2013

(86) PCT No.: PCT/US2013/068741
§ 371 (c)(1),
(2) Date: May 6, 2015

(87) PCT Pub. No.: WO2014/074597
PCT Pub. Date: May 15, 2014

(65) Prior Publication Data
US 2015/0329584 A1  Nov. 19, 2015

Related U.S. Application Data

(60) Provisional application No. 61/722,823, filed on Nov. 6, 2012.

(51) Int. Cl.
| | | |
|---|---|---|
| C07H 21/04 | (2006.01) | |
| C07H 1/00 | (2006.01) | |
| C12N 15/10 | (2006.01) | |

(52) U.S. Cl.
CPC .............. *C07H 21/04* (2013.01); *C07H 1/00* (2013.01); *C12N 15/10* (2013.01); *C12N 15/1031* (2013.01)

(58) Field of Classification Search
CPC .......... C07H 1/00; C07H 21/04; C12N 15/10; C12N 15/1031
USPC ........................................... 435/6.1; 536/23.1
See application file for complete search history.

(56) References Cited

U.S. PATENT DOCUMENTS

| | | | |
|---|---|---|---|
| 5,386,020 | A  | 1/1995 | Seeman et al. |
| 6,255,469 | B1 | 7/2001 | Seeman et al. |
| 6,444,650 | B1 | 9/2002 | Cech et al. |
| 6,444,661 | B1 | 9/2002 | Barton et al. |
| 7,745,594 | B2 | 6/2010 | Seelig et al. |
| 7,842,793 | B2 | 11/2010 | Rothemund |
| 8,877,438 | B2 | 11/2014 | Yin |
| 2003/0219790 | A1 | 11/2003 | Seeman et al. |
| 2006/0078910 | A1 | 4/2006 | Seeman et al. |
| 2007/0117109 | A1 | 5/2007 | Rothemund |
| 2007/0238096 | A1 | 10/2007 | Reich et al. |
| 2008/0221315 | A1 | 9/2008 | Garibotti et al. |
| 2009/0227774 | A1 | 9/2009 | Turberfield et al. |
| 2010/0216978 | A1 | 8/2010 | Shih |
| 2010/0291485 | A1 | 11/2010 | Lapsys et al. |
| 2011/0033706 | A1 | 2/2011 | Krishnan |
| 2012/0022244 | A1 | 1/2012 | Yin et al. |
| 2012/0251583 | A1* | 10/2012 | Rothemund ............ C12P 19/34 424/400 |
| 2013/0065777 | A1 | 3/2013 | Altug et al. |
| 2013/0316358 | A1 | 11/2013 | Navon et al. |
| 2014/0213778 | A1 | 7/2014 | Yin et al. |
| 2015/0218204 | A1 | 8/2015 | Yin et al. |
| 2017/0015698 | A1 | 1/2017 | Iinuma et al. |
| 2017/0190573 | A1 | 7/2017 | Shen et al. |

FOREIGN PATENT DOCUMENTS

| | | |
|---|---|---|
| CN | 1390253 A | 1/2003 |
| JP | 2004-510780 A | 4/2004 |
| JP | 2008-504846 A | 2/2008 |
| WO | WO 01/36624 A1 | 5/2001 |
| WO | WO 2005/024018 A1 | 3/2005 |
| WO | WO 2006/017432 A2 | 2/2006 |
| WO | WO 2007/012807 A2 | 2/2007 |
| WO | WO 2009/043184 A1 | 4/2009 |
| WO | WO 2009/093558 A1 | 7/2009 |
| WO | WO 2012/058638 A2 | 5/2012 |
| WO | WO 2013/022694 A1 | 2/2013 |
| WO | WO 2013/088098 A2 | 6/2013 |
| WO | WO 2014/018675 A1 | 1/2014 |
| WO | WO 2014/074597 A1 | 5/2014 |

OTHER PUBLICATIONS

Yin et al., Science., vol. 321, pp. 824-826, Aug. 2008.*
Seeman, N.C., Nature., vol. 421, pp. 427-431, 2003.*
Tumpane et al., Nano Letter, 2007, 7 (12), pp. 3832-3839.*
U.S. Appl. No. 14/237,001, filed Mar. 31, 2014, Allowed, 2014-0213778.
U.S. Appl. No. 14/417,390, filed Jan. 26, 2015, Published, 2015-0218204.
U.S. Appl. No. 15/312,854, filed Nov. 21, 2016, Published, 2017-0190573.
U.S. Appl. No. 15/124,066, filed Sep. 7, 2016, Published, 2017-0015698.
EP 12821431.9, Mar. 5, 2015, Extended European Search Report.

(Continued)

*Primary Examiner* — Cynthia B Wilder
(74) *Attorney, Agent, or Firm* — Wolf, Greenfield & Sacks, P.C.

(57) ABSTRACT

The invention provides SST motifs of controlled size and shape, comprised of a plurality of oligonucleotides, and methods for their synthesis. The motifs are formed, at least in part, by the self-assembly of single stranded oligonucleotides into curved, corrugated or twisted structures. The location of each oligonucleotide in the resultant motif is known. Accordingly, the motifs may be modified with specificity.

26 Claims, 9 Drawing Sheets

(56) References Cited

OTHER PUBLICATIONS

PCT/US2012/049306, Nov. 22, 2012, International Search Report and Written Opinion.
PCT/US2012/049306, Feb. 20, 2014, International Preliminary Report on Patentability.
PCT/US2013/051891, Oct. 25, 2013, International Search Report and Written Opinion.
PCT/US2013/051891, Feb. 5, 2015, International Preliminary Report on Patentability.
PCT/US2013/068741, Feb. 20, 2014, International Search Report and Written Opinion.
PCT/US2013/068741, May 21, 2015, International Preliminary Report on Patentability.
PCT/US2015/032198, Dec. 11, 2015, International Search Report and Written Opinion.
PCT/US2015/032198, Dec. 1, 2016, International Preliminary Report on Patentability.
EP 15761059.3, Jul. 4, 2017, Extended European Search Report.
PCT/US2015/019135, Jun. 9, 2015, International Search Report and Written Opinion.
PCT/US2015/019135, Sep. 22, 2016, International Preliminary Report on Patentability.
PCT/US2016/020893, May 31, 2016, International Search Report and Written Opinion.
Acuna et al., Fluorescence enhancement at docking sites of DNA-directed self-assembled nanoantennas. Science. Oct. 26, 2012;338(6106):506-10. doi:10.1126/science.1228638.
Aldaye et al., Assembling materials with DNA as the guide. Science. Sep. 26, 2008;321(5897):1795-9. doi: 10.1126/science.1154533.
Aldaye et al., Modular access to structurally switchable 3D discrete DNA assemblies. J Am Chem Soc. Nov. 7, 2007;129(44):13376-7. Epub Oct. 16, 2007.
Aldaye et al., Sequential self-assembly of a DNA hexagon as a template for the organization of gold nanoparticles. Angew Chem Int Ed Engl. Mar. 27, 2006;45(14):2204-9.
Alexander et al., On Types of Knotted Curves. Annals of Mathematics 1926-1927, 28(1/4): 562-586.
Alexander, Topical Invariants of Knots and Links. Transactions of the American Mathematical Society 1928, 30(2): 275-306.
Andersen et al., Self-assembly of a nanoscale DNA box with a controllable lid. Nature. May 7, 2009;459(7243):73-6. doi:10.1038/nature07971.
Anthony, MIT and Harvard engineers create graphene electronics with DNA based lithography. Extremetech.com. Apr. 10, 2013. http://www.extremetech.com/computing/153046-mit-and-harvard-engineers-create-graphene-electronics-with-dna-based-lithography.
Barish et al., An information-bearing seed for nucleating algorithmic self-assembly. Proc Natl Acad Sci U S A. Apr. 14, 2009;106(15):6054-9. doi: 10.1073/pnas.0808736106. Epub Mar. 24, 2009.
Bath et al., DNA nanomachines. Nat Nanotechnol. May 2007;2(5):275-84. doi:10.1038/nnano.2007.104.
Berardi et al., Mitochondrial uncoupling protein 2 structure determined by NMR molecular fragment searching. Nature. Jul. 24, 2011;476(7358):109-13. doi: 10.1038/nature10257.
Bertrand et al., Flexibility of the B-DNA backbone: effects of local and neighbouring sequences on pyrimidine-purine steps. Nucleic Acids Res. Mar. 1, 1998;26(5):1261-7.
Bhatia et al., Icosahedral DNA nanocapsules by modular assembly. Angew Chem Int Ed Engl. 2009;48(23):4134-7.doi:10.1002/anie.200806000.
Cataldo et al., DNA degradation with ozone. Int J Biol Macromol. May 30, 2006;38(3-5):248-54. Epub Apr. 17, 2006.
Chen et al., DNA-directed assembly of single-wall carbon nanotubes. J Am Chem Soc. Jul. 18, 2007;129(28):8696-7. Epub Jun. 23, 2007.

Chen et al., Invadable self-assembly: combining robustness with efficiency. Proceeding SODA '04 Proceedings of the fifteenth annual ACM-SIAM symposium on Discrete algorithms. 2004:890-9.
Chen et al., Synthesis from DNA of a molecule with the connectivity of a cube. Nature. Apr. 18, 1991;350(6319):631-3.
Choi et al., Programmable in situ amplification for multiplexed imaging of mRNA expression. Nat Biotechnol. Nov. 2010;28(11):1208-12. doi: 10.1038/nbt.1692. Epub Oct. 31, 2010.
Chworos et al., Building programmable jigsaw puzzles with RNA. Science. Dec. 17, 2004;306(5704):2068-72.
Delebecque et al., Organization of intracellular reactions with rationally designed RNA assemblies. Science. Jul. 22, 2011;333(6041):470-4. doi: 10.1126/science.1206938. Epub Jun. 23, 2011.
Dietz et al., Folding DNA into twisted and curved nanoscale shapes. Science. Aug. 7, 2009;325(5941):725-30. doi: 10.1126/science.1174251.
Dimitrakakis et al., Top-down patterning of zeolitic imidazolate framework composite thin films by deep X-ray lithography. Chem Commun (Camb). Aug. 4, 2012;48(60):7483-5. doi: 10.1039/c2cc33292b. Epub Jun. 22, 2012.
Douglas et al., A logic-gated nanorobot for targeted transport of molecular payloads. Science. Feb. 17, 2012;335(6070):831-4. doi:10.1126/science.1214081.
Douglas et al., DNA-nanotube-induced alignment of membrane proteins for NMR structure determination. Proc Natl Acad Sci U S A. Apr. 17, 2007;104(16):6644-8. Epub Apr. 2, 2007.
Douglas et al., Rapid prototyping of 3D DNA-origami shapes with caDNAno. Nucleic Acids Res. Aug. 2009;37(15):5001-6. doi: 10.1093/nar/gkp436. Epub Jun. 16, 2009.
Douglas et al., Self-assembly of DNA into nanoscale three-dimensional shapes. Nature. May 21, 2009;459(7245):414-8.doi: 10.1038/nature08016.
Erben et al., A self-assembled DNA bipyramid. J Am Chem Soc. Jun. 6, 2007;129(22):6992-3. Epub May 15, 2007.
Feldkamp et al., Rational design of DNA nanoarchitectures. Angew Chem Int Ed Engl. Mar. 13, 2006;45(12):1856-76.
Fratini et al., Reversible bending and helix geometry in a B-DNA dodecamer: CGCGAATTBrCGCG. J Biol Chem. Dec. 25, 1982;257(24):14686-707.
Fu et al., DNA double-crossover molecules. Biochemistry. Apr. 6, 1993;32(13):3211-20.
Fu et al., Interenzyme substrate diffusion for an enzyme cascade organized on spatially addressable DNA nanostructures. J Am Chem Soc. Mar. 28, 2012;134(12):5516-9. doi:10.1021/ja300897h. Epub Mar. 16, 2012.
Geary et al., A single-stranded architecture for cotranscriptional folding of RNA nanostructures. Science. Aug. 15, 2014;345(6198):799-804. doi: 10.1126/science.1253920.
Goodman et al., Rapid chiral assembly of rigid DNA building blocks for molecular nanofabrication. Science. Dec. 9, 2005;310(5754):1661-5.
Goodman et al., Reconfigurable, braced, three-dimensional DNA nanostructures. Nat Nanotechnol. Feb. 2008;3(2):93-6. doi: 10.1038/nnano.2008.3. Epub Feb. 3, 2008.
Han et al., DNA gridiron nanostructures based on four-arm junctions. Science. Mar. 22, 2013;339(6126):1412-5. doi: 10.1126/science.1232252.
Han et al., DNA origami with complex curvatures in three-dimensional space. Science. Apr. 15, 2011;332(6027):342-6. doi:10.1126/science.1202998.
Han et al., Folding and cutting DNA into reconfigurable topological nanostructures. Nat Nanotechnol. Oct. 2010;5(10):712-7. doi:10.1038/nnano.2010.193. Epub Oct. 3, 2010.
Han et al., Unidirectional scaffold-strand arrangement in DNA origami. Angew Chem Int Ed Engl. Aug. 19, 2013;52(34):9031-4. doi: 10.1002/anie.201302177. Epub Jul. 14, 2013.
Hansma et al., DNA binding to mica correlates with cationic radius:assay by atomic force microscopy. Biophys J. Apr. 1996;70(4):1933-9.

(56) References Cited

OTHER PUBLICATIONS

He et al., Hierarchical self-assembly of DNA into symmetric supramolecular polyhedra. Nature. Mar. 13, 2008;452(7184):198-201. doi: 10.1038/nature06597.

Hell, Far-field optical nanoscopy. Science. May 25, 2007;316(5828):1153-8.

Horiya et al., RNA LEGO: magnesium-dependent formation of specific RNA assemblies through kissing interactions. Chem Biol. Jul. 2003;10(7):645-54.

Huang et al., Three-dimensional super-resolution imaging by stochastic optical reconstruction microscopy. Science. Feb. 8, 2008;319(5864):810-3. doi: 10.1126/science.1153529. Epub Jan. 3, 2008.

Iinuma et al., Polyhedra self-assembled from DNA tripods and characterized with 3D DNA-PAINT. Science. Apr. 4, 2014;344(6179):65-9. doi: 10.1126/science.1250944. Epub Mar. 13, 2014.

Jin et al., Metallized DNA nanolithography for encoding and transferring spatial information for graphene patterning. Nat Commun. 2013;4:1663. doi: 10.1038/ncomms2690.

Jones et al., Nanomaterials. Programmable materials and the nature of the DNA bond. Science. Feb. 20, 2015;347(6224):1260901. doi:10.1126/science.1260901.

Jungmann et al., DNA origami-based nanoribbons: assembly, length distribution, and twist. Nanotechnology. Jul. 8, 2011;22(27):275301. doi: 10.1088/0957-4484/22/27/275301. Epub May 20, 2011.

Jungman et al., Multiplexed 3D cellular super-resolution imaging with DNA-PAINT and Exchange-PAINT. Nat Methods. Mar. 2014;11(3):313-8. doi: 10.1038/nmeth.2835. Epub Feb. 2, 2014.

Jungmann et al., Single-molecule kinetics and super-resolution microscopy by fluorescence imaging of transient binding on DNA origami. Nano Lett. Nov. 10, 2010;10(11):4756-61. doi:10.1021/nl103427w.

Jonoska et al., Blueprints for dodecahedral DNA cages. J Phys A: Math Theor. Aug. 1, 2008;41(30):304043(1-14).

Kao et al., Tracking of single fluorescent particles in three dimensions: use of cylindrical optics to encode particle position. Biophys J. Sep. 1994;67(3):1291-300.

Ke et al., A study of DNA tube formation mechanisms using 4-, 8-, and 12-helix DNA nanostructures. J Am Chem Soc. Apr. 5, 2006;128(13):4414-21.

Ke et al., DNA brick crystals with prescribed depths. Nat Chem. Nov. 2014;6(11):994-1002. doi: 10.1038/nchem.2083. Epub Oct. 19, 2014.

Ke et al., Multilayer DNA origami packed on a square lattice. J Am Chem Soc. Nov. 4, 2009;131(43):15903-8. doi:10.1021/ja906381y.

Ke et al., Multilayer DNA origami packed on hexagonal and hybrid lattices. J Am Chem Soc. Jan. 25, 2012;134(3):1770-4. doi:10.1021/ja209719k. Epub Jan. 13, 2012.

Ke et al., Scaffolded DNA origami of a DNA tetrahedron molecular container. Nano Lett. Jun. 2009;9(6):2445-7. doi:10.1021/nl901165f.

Ke et al., Three-dimensional structures self-assembled from DNA bricks. Science. Nov. 30, 2012;338(6111):1177-83. doi: 10.1126/science.1227268.

Ke, Designer three-dimensional DNA architectures. Curr Opin Struct Biol. Aug. 2014;27:122-8. doi: 10.1016/j.sbi.2014.07.010. Epub Aug. 11, 2014.

Killops et al., Robust, efficient, and orthogonal synthesis of dendrimers via thiol-ene "click" chemistry. J Am Chem Soc. Apr. 16, 2008;130(15):5062-4. doi: 10.1021/ja8006325. Epub Mar. 20, 2008.

Kuzuya et al., DNA origami: fold, stick, and beyond. Nanoscale. Mar. 2010;2(3):310-22. doi: 10.1039/b9nr00246d. Epub Nov. 24, 2009.

Kuzuya et al., Six-helix and eight-helix DNA nanotubes assembled from half-tubes. Nano Lett. Jun. 2007;7(6):1757-63. Epub May 15, 2007.

Kuzyk et al., DNA-based self-assembly of chiral plasmonic nanostructures with tailored optical response. Nature. Mar. 14, 2012;483(7389):311-4. doi:10.1038/nature10889.

Langecker et al., Synthetic lipid membrane channels formed by designed DNA nanostructures. Science. Nov. 16, 2012;338(6109):932-6. doi: 10.1126/science.1225624.

Le et al., DNA-Templated Self-Assembly of Metallic Nanocomponent Arrays on a Surface. Nano Lett. 2004;4(12):2343-7.

Lee et al., Rate and molecular spectrum of spontaneous mutations in the bacterium *Escherichia coli* as determined by whole-genome sequencing. Proc Natl Acad Sci U S A. Oct. 9, 2012;109(41):E2774-83. doi: 10.1073/pnas.1210309109. Epub Sep. 18, 2012.

Leontis et al., Self-assembled RNA nanostructures. Science. Aug. 15, 2014;345(6198):732-3. doi:10.1126/science.1257989.

Li et al., A replicable tetrahedral nanostructure self-assembled from a single DNA strand. J Am Chem Soc. Sep. 16, 2009;131(36):13093-8. doi: 10.1021/ja903768f.

Li et al., Nucleic acid-based nanoengineering: novel structures for biomedical applications. Interface Focus. Oct. 6, 2011;1(5):702-24. doi: 10.1098/rsfs.2011.0040. Epub Jun. 28, 2011.

Li et al., Single-chain antibodies against DNA aptamers for use as adapter molecules on DNA tile arrays in nanoscale materials organization. Org Biomol Chem. Sep. 21, 2006;4(18):3420-6. Epub Jul. 28, 2006.

Liedl et al., Self-assembly of three-dimensional prestressed tensegrity structures from DNA. Nat Nanotechnol. Jul. 2010;5(7):520-4. doi: 10.1038/nnano.2010.107. Epub Jun. 20, 2010.

Lin et al., DNA tile based self-assembly: building complex nanoarchitectures. Chemphyschem. Aug. 11, 2006;7(8):1641-7.

Lin et al., In vivo cloning of artificial DNA nanostructures. Proc Natl Acad Sci U S A. Nov. 18, 2008;105(46):17626-31. doi: 10.1073/pnas.0805416105. Epub Oct. 16, 2008.

Lin et al., Mirror image DNA nanostructures for chiral supramolecular assemblies. Nano Lett. Jan. 2009;9(1):433-6. doi:10.1021/n1803328v.

Lin et al., Submicrometre geometrically encoded fluorescent barcodes self-assembled from DNA. Nat Chem. 2012;4:832-9.

Linko et al., The enabled state of DNA nanotechnology. Gun Opin Biotechnol. Aug. 2013;24(4):555-61. doi: 10.1016/j.copbio.2013.02.001. Epub Apr. 6, 2013.

Liu et al., Approaching the limit: can one DNA oligonucleotide assemble into large nanostructures? Angew Chem Int Ed Engl. Mar. 13, 2006;45(12):1942-5.

Liu et al., Crystalline two-dimensional DNA-origami arrays. Angew Chem Int Ed Engl. Jan. 3, 2011;50(1):278-81. doi:10.1002/anie.201005911.

Liu et al., DNA nanotubes self-assembled from triple-crossover tiles as templates for conductive nanowires. Proc Natl Acad Sci U S A. Jan. 20, 2004;101(3):717-22. Epub Jan. 6, 2004.

Liu et al., Tensegrity: construction of rigid DNA triangles with flexible four-arm DNA junctions. J Am Chem Soc. Mar. 3, 2004;126(8):2324-5.

Liu et al., Three-dimensional plasmon rulers. Science. Jun. 17, 2011;332(6036):1407-10. doi:10.1126/science.1199958.

Ma et al., Biotemplated nanostructures: directed assembly of electronic and optical materials using nanoscale complementarity. Journal of Materials Chemistry. 2008;18(9):954-64.

Mansfield, Are there knots in proteins? Nat Struct Biol. Apr. 1994;1(4):213-4.

Mao et al, Designed Two-Dimensional DNA Holliday Junction Arrays Visualized by Atomic Force Microscopy. J. Am. Chem. Soc., 1999, 121 (23), pp. 5437-5443.

Marchi et al., Toward larger DNA origami. Nano Lett. Oct. 8, 2014;14(10):5740-7. doi: 10.1021/n1502626s. Epub Sep. 8, 2014.

Mathieu et al., Six-helix bundles designed from DNA. Nano Lett. Apr. 2005;5(4):661-5.

Matsui et al., Focused ion beam applications to solid state devices. Nanotechnology 1996, 7(3):247.

Melosh et al., Ultrahigh-density nanowire lattices and circuits. Science. Apr. 4, 2003;300(5616):112-5. Epub Mar. 13, 2003.

(56) References Cited

OTHER PUBLICATIONS

Mitchell et al., Self-assembly of chiral DNA nanotubes. J Am Chem Soc. Dec. 22, 2004;126(50):16342-3.
Monson et al., DNA-Templated Constructed of Copper Nanowires. Nano Letters. 2003;3(2):359-63. Epub Feb. 14, 2003.
Nie et al., Self-assembly of DNA nanoprisms with only two component strands. Chem Commun (Camb). Apr. 7, 2013;49(27):2807-9. doi:10.1039/c3cc39177a.
Oliveira et al., Structure of nanoscale truncated octahedral DNA cages: Variation of single-stranded linker regions and influence on assembly yields. ACS Nano. Mar. 23, 2010;4(3):1367-76.
O'Neill et al., Sturdier DNA nanotubes via ligation. Nano Lett. Jul. 2006;6(7):1379-83.
Park et al., Finite-size, fully addressable DNA tile lattices formed by hierarchical assembly procedures. Angew Chem Int Ed Engl. Jan. 23, 2006;45(5):735-9. Erratum in: Angew Chem Int Ed Engl. Oct. 13, 2006;45(40):6607.
Park et al., Programmable DNA self-assemblies for nanoscale organization of ligands and proteins. Nano Lett. Apr. 2005;5(4):729-33.
Park et al., Three-helix bundle DNA tiles self-assemble into 2D lattice or 1D templates for silver nanowires. Nano Lett. Apr. 2005;5(4):693-6.
Petty et al., DNA-templated Ag nanocluster formation. J Am Chem Soc. Apr. 18, 2004;126(16):5207-12.
Pieles et al., Psoralen covalently linked to oligodeoxyribonucleotides: synthesis, sequence specific recognition of DNA and photo-cross-linking to pyrimidine residues of DNA. Nucleic Acids Res. Jan. 11, 1989;17(1):285-99.
Piner et al,. "Dip-Pen" nanolithography. Science. Jan. 29, 1999;283(5402):661-3.
Pinheiro et al., Challenges and opportunities for structural DNA nanotechnology. Nat Nanotechnol. Nov. 6, 2011;6(12):763-72. doi:10.1038/nnano.2011.187.
Qi et al., A three-dimensional optical photonic crystal with designed point defects. Nature. Jun. 3, 2004;429(6991):538-42.
Qian et al., Scaling up digital circuit computation with DNA strand displacement cascades. Science. Jun. 3, 2011;332(6034):1196-201. doi:10.1126/science.1200520.
Rajendran et al., Photo-cross-linking-assisted thermal stability of DNA origami structures and its application for higher-temperature self-assembly. J Am Chem Soc. Sep. 21, 2011;133(37):14488-91. doi:10.1021/ja204546h. Epub Aug. 29, 2011.
Rajesh et al,. Carbon Nanotubes Generated from Template Carbonization of Polyphenyl Acetylene as the Support for Electrooxidation of Methanol. J. Phys. Chem. B, 2003, 107 (12), pp. 2701-2708.
Randolph et al., Focused, Nanoscale Electron-Beam-Induced Deposition and Etching. Critical Reviews in Solid State and Material Sciences, 2006, 31(3):55-89.
Ravanat et al., Direct and indirect effects of UV radiation on DNA and its components. J Photochem Photobiol B. Oct. 2001;63(1-3):88-102.
Reif et al., Compact error-resilient computational DNA tiling assemblies. Proceeding DNA'04 Proceedings of the 10th international conference on DNA computing. 2004:293-307.
Reif et al., Complexity of graph self-assembly in accretive systems and self-destructible systems. Journal Theoretical Computer Science. 2011;412(17):1592-605.
Rothemund et al., Algorithmic Self-Assembly of DNA Sierpinski Triangles. PLoS Biology. 2004. 2004;2(12):e424. doi:10.1371/journal.pbio.0020424.
Rothemund et al., Design and characterization of programmable DNA nanotubes. J Am Chem Soc. Dec. 22, 2004;126(50):16344-52. Erratum in: J Am Chem Soc. Feb. 20, 2013;135(7):2864.
Rothemund et al., The program-size complexity of self-assembled squares. Extended Abstract. Proceeding STOC '00 Proceedings of the thirty-second annual ACM symposium on Theory of computing. ACM 2000:459-68.
Rothemund, Folding DNA to create nanoscale shapes and patterns. Nature. Mar. 16, 2006;440(7082):297-302.

Sahu et al., A self-assembly model of time-dependent glue strength. DNA'05 Proceedings of the 11th international conference on DNA Computing. 2005:290-304.
Scheible et al., A Compact DNA Cube with Side Length 10 nm. Small. Oct. 21, 2015;11(39):5200-5. doi: 10.1002/smll.201501370. Epub Aug. 21, 2015.
Schmied et al., DNA origami nanopillars as standards for three-dimensional superresolution microscopy. Nano Lett. Feb. 13, 2013;13(2):781-5. doi: 10.1021/nl304492y. Epub Feb. 5, 2013.
Schulman et al., Synthesis of crystals with a programmable kinetic barrier to nucleation. Proc Natl Acad Sci U S A. Sep. 25, 2007;104(39):15236-41. Epub Sep. 19, 2007.
Schweller et al., Multiplexed in situ immunofluorescence using dynamic DNA complexes. Angew Chem Int Ed Engl. Sep. 10, 2012;51(37):9292-6. doi: 10.1002/anie.201204304. Epub Aug. 15, 2012.
Seelig et al., Enzyme-free nucleic acid logic circuits. Science. Dec. 8, 2006;314(5805):1585-8.
Seeman et al., Nucleic acid nanostructures: Bottom-up control of geometry on the nanoscale. Rep. Prog. Phys, 2005, 68: 237-70.
Seeman et al., The design and engineering of nucleic acid nanoscale assemblies. Curr Opin Struct Biol. Aug. 1996;6(4):519-26.
Seeman, De novo design of sequences for nucleic acid structural engineering. J Biomol Struct Dyn. Dec. 1990;8(3):573-81.
Seeman, DNA in a material world. Nature. Jan. 23, 2003;421(6921):427-31.
Seeman, Nanomaterials based on DNA. Annu Rev Biochem. 2010;79:65-87. doi:10.1146/annurev-biochem-060308-102244.
Seeman, Nucleic acid junctions and lattices. J Theor Biol. Nov. 21, 1982;99(2):237-47.
Sekulić et al., A direct linkage between the phosphoinositide 3-kinase-AKT signaling pathway and the mammalian target of rapamycin in mitogen-stimulated and transformed cells. Cancer Res. Jul. 1, 2000;60(13):3504-13.
Sharma et al., Control of self-assembly of DNA tubules through integration of gold nanoparticles. Science. Jan. 2, 2009;323(5910):112-6. doi: 10.1126/science.1165831.
Sharma et al., DNA-tile-directed self-assembly of quantum dots into two-dimensional nanopatterns. Angew Chem Int Ed Engl. 2008;47(28):5157-9. doi:10.1002/anie.200801485.
Sharma et al., Toward reliable gold nanoparticle patterning on self-assembled DNA nanoscaffold. J Am Chem Soc. Jun. 25, 2008;130(25):7820-1. doi: 10.1021/ja802853r. Epub May 30, 2008.
Sharonov et al., Wide-field subdiffraction imaging by accumulated binding of diffusing probes. Proc Natl Acad Sci USA. Dec. 12, 2006;103(50):18911-6. Epub Dec. 1, 2006.
Sherman et al., A Precisely Controlled DNA Biped Walking Device. Nano Letters. 2004;4(7):1203-7.
Shih et al., A 1.7-kilobase single-stranded DNA that folds into a nanoscale octahedron. Nature. Feb. 12, 2004;427(6975):618-21.
Shih et al., Knitting complex weaves with DNA origami. Curr Opin Struct Biol. Jun. 2010;20(3):276-82. doi: 10.1016/j.sbi.2010.03.009. Epub Apr. 22, 2010.
Shtengel et al., Interferometric fluorescent super-resolution microscopy resolves 3D cellular ultrastructure. Proc Natl Acad Sci U S A. Mar. 3, 2009;106(9):3125-30. doi:10.1073/pnas.0813131106. Epub Feb. 6, 2009.
Smith et al., A structurally variable hinged tetrahedron framework from DNA origami. J Nucleic Acids. 2011;2011:360954. doi: 10.4061/2011/360954. Epub Sep. 18, 2011.
Surwade et al., Molecular lithography through DNA-mediated etching and masking of SiO2. J Am Chem Soc. Aug. 10, 2011;133(31):11868-71. doi: 10.1021/ja2038886. Epub Jul. 19, 2011.
Surwade et al., Nanoscale growth and patterning of inorganic oxides using DNA nanostructure templates. J Am Chem Soc. May 8, 2013;135(18):6778-81. doi: 10.1021/ja401785h. Epub Apr. 25, 2013.
Takusagawa et al., A Real Knot in Protein. J. Am. Chem. Soc., 1996, 118 (37), pp. 8945-8946.
Tang et al., Evolution of block copolymer lithography to highly ordered square arrays. Science. Oct. 17, 2008;322(5900):429-32. doi: 10.1126/science.1162950. Epub Sep. 25, 2008.

(56) References Cited

OTHER PUBLICATIONS

Tavakkoli et al., Templating three-dimensional self-assembled structures in bilayer block copolymer films. Science. Jun. 8, 2012;336(6086):1294-8. doi: 10.1126/science.1218437.

Taylor, A deeply knotted protein structure and how it might fold. Nature. Aug. 24, 2000;406(6798):916-9.

Tørring et al., DNA origami: a quantum leap for self-assembly of complex structures. Chem Soc Rev. Dec. 2011;40(12):5636-46. doi: 10.1039/c1cs15057j. Epub May 19, 2011.

Venkataraman et al., Selective cell death mediated by small conditional RNAs. Proc Natl Acad Sci USA. Sep. 28, 2010;107(39):16777-82. doi: 10.1073/pnas.1006377107. Epub Sep. 7, 2010. Retraction in: Dirks RM, Ueda CT, Pierce NA. Proc Natl Acad Sci U S A. Jan. 2, 2013;110(1):384.

Wagner et al., A light-sensing knot revealed by the structure of the chromophore-binding domain of phytochrome. Nature. Nov. 17, 2005;438(7066):325-31.

Wei et al., Complex shapes self-assembled from single-stranded DNA tiles. Nature. May 30, 2012;485(7400):623-6. doi: 10.1038/nature11075.

Wei et al., Uniquimer: Software of De Novo DNA Sequence Generation for DNA Self-Assembly—An Introduction and the Related Applications in DNA Self-Assembly. J Comput Theor Nanosci. 2007;4(1):133-41.

Williams et al,. Tiamat: A Three-Dimensional Editing Tool for Complex DNA Structures. DNA Computing 2009, 90-101.

Winfree et al., Design and self-assembly of two-dimensional DNA crystals. Nature. Aug. 6, 1998;394(6693):539-44.

Winfree, Algorithmic Self-Assembly of DNA. Doctoral Thesis. California Institute of Technology. Mar. 1998.

Winters et al., Surface science aspects of etching reactions. Surface Science Reports. 1992, 14(4-6): 162-269.

Woo et al., Programmable molecular recognition based on the geometry of DNA nanostructures. Nat Chem. Jul. 10, 2011;3(8):620-7. doi: 10.1038/nchem.1070. Erratum in: Nat Chem. Oct. 2011;3(10):829. Nat Chem. 2011;3(8):following 627.

Wu et al., High aspect ratio silicon etch: A review. Journal of Applied Physics, 2010, 108(5): 051101-051101-20.

Xiao et al., Self-assembly of Metallic Nanoparticle Arrays by DNA Scaffolding. Journal of Nanoparticle Research. Aug. 1, 2002;4:313-7.

Yan et al., A robust DNA mechanical device controlled by hybridization topology. Nature. Jan. 3, 2002;415(6867):62-5.

Yan et al., Directed nucleation assembly of DNA tile complexes for barcode-patterned lattices. Proc Natl Acad Sci U S A. Jul. 8, 2003;100(14):8103-8. Epub Jun. 23, 2003.

Yan et al., DNA-templated self-assembly of protein arrays and highly conductive nanowires. Science. Sep. 26, 2003;301(5641):1882-4.

Yang et al., DNA Origami with Double-Stranded DNA as a Unified Scaffold. ACS Nano, 2012, 6(9): 8209-8215.

Yang et al., Metal-nucleic acid cages. Nat Chem. Aug. 2009;1(5):390-6. doi: 10.1038/nchem.290.

Yevdokimov et al., Nanoconstructions based on double-stranded nucleic acids. Int J Biol Macromol. Jul. 2005;36(1-2):103-15.

Yin et al., A unidirectional DNA walker that moves autonomously along a track. Angew Chem Int Ed Engl. Sep. 20, 2004;43(37):4906-11.

Yin et al., Designs of autonomous unidirectional walking DNA devices. Proceeding DNA'04 Proceedings of the 10th international conference on DNA computing. 2004:410-25.

Yin et al., Programming biomolecular self-assembly pathways. Nature. Jan. 17, 2008;451(7176):318-22. doi: 10.1038/nature06451.

Yin et al., Programming DNA tube circumferences. Science. Aug. 8, 2008;321(5890):824-6.

Yin et al., Theoretical and practical advances in genome halving. Bioinformatics. Apr. 1, 2005;21(7):869-79. Epub Oct. 28, 2004.

Yurke et al., A DNA-fueled molecular machine made of DNA. Nature. Aug. 10, 2000;406(6796):605-8.

Zhang et al., Conformational flexibility facilitates self-assembly of complex DNA nanostructures. Proc Natl Acad Sci U S A. Aug. 5, 2008;105(31):10665-9. doi:10.1073/pnas.0803841105. Epub Jul. 30, 2008.

Zhang et al., DNA self-assembly: from 2D to 3D. Faraday Discussions. Jul. 27, 2009;143:221-33.

Zhang et al., Construction of a DNA-Truncated Octahedron. J Am Chem Soc 1994;116(5):1661-9.

Zhang et al., Structural DNA nanotechnology: state of the art and future perspective. J Am Chem Soc. Aug. 13, 2014;136(32):11198-211. doi:10.1021/ja505101a. Epub Jul. 28, 2014.

Zhang et al., Symmetry controls the face geometry of DNA polyhedra. J Am Chem Soc. Feb. 4, 2009;131(4):1413-5. doi:10.1021/ja809666h.

Zhao et al., Organizing DNA origami tiles into larger structures using preformed scaffold frames. Nano Lett. Jul. 13, 2011;11(7):2997-3002. doi:10.1021/nl201603a. Epub Jun. 23, 2011.

Zheng et al., From molecular to macroscopic via the rational design of a self-assembled 3D DNA crystal. Nature. Sep. 3, 2009;461(7260):74-7. doi:10.1038/nature08274.

Zimmermann et al., Self-assembly of a DNA dodecahedron from 20 trisoligonucleotides with C(3h) linkers. Angew Chem Int Ed Engl. 2008;47(19):3626-30. doi: 10.1002/anie.200702682.

\* cited by examiner

FIG. 5B

COMPOSITIONS AND METHODS RELATING TO COMPLEX NUCLEIC ACID NANOSTRUCTURES

RELATED APPLICATIONS

This application is a national stage filing under 35 U.S.C. § 371 of international application number PCT/US2013/068741, filed Nov. 6, 2013, which was published under PCT Article 21(2) in English and claims the benefit under 35 U.S.C. § 119(e) of U.S. provisional application No. 61/722,823, filed Nov. 6, 2012, each of which is incorporated by reference herein in its entirety.

FEDERALLY SPONSORED RESEARCH

This invention was made with Government support under OD007292 awarded by National Institutes of Health, and under CCF-1054898 awarded by National Science Foundation, and under N00014-10-1-0827 awarded by Department of Defense. The Government has certain rights in the invention.

BACKGROUND OF INVENTION

The field of nucleic acid nanotechnology has rapidly grown from simple junction formation of just a few synthesized strands to complex interacting systems with hundreds of de novo designed and synthesized, self-assembling strands.

Most of the early development of structural nucleic acid nanotechnology is based on so-called DNA tiles, which are individual, rigid DNA complexes composed of multiple, single stranded DNA with crossovers. The complexity of the traditional tiling approach was improved by the introduction of a DNA origami approach, in which short synthetic DNA strands are globally coordinated by a single information-barring scaffold to form nucleic acid structures en masse.

More recent work with single stranded oligonucleotide offers more complex nucleic acid structures through the synthesis of extended sizes and the use of combinatorial expression patterns.

SUMMARY OF INVENTION

The invention provides, inter alia, methods for making nucleic acid structures (referred to herein as single stranded tile (SST) motifs) of known and predetermined and thus controlled size, shape and complexity, as well as the nucleic acid structures themselves. The SST motifs of the invention are directed to self-assemble through hybridization of single stranded oligonucleotide domains of predetermined sequence and length. By adjusting various structural parameters, including oligonucleotide domain length and distance between adjacent crossovers, the surface curvature, twist and structural rigidity of the SST motifs can be controlled. For example, the local curvature and twist of assembled SST motifs of the invention can be controlled by altering lengths of complementary single stranded oligonucleotide domains and by altering interhelical crossover patterns. Further, by altering the orientation and connection patterns between single stranded oligonucleotides, it is possible to attach (e.g., ligate) linkers such as, for example, poly T linkers of different lengths to oligonucleotides of the SST motifs, thereby improving structural integrity.

The SST motifs of the invention are made by binding a plurality of single stranded oligonucleotides to each other in a sequence-specific manner, with or without stabilizing linkers. The SST motifs and the single stranded oligonucleotides are designed so that the location of each oligonucleotide in each motif is known, and accordingly so that the nucleotide sequence at each location in the SST motif is known. The ability to know the location of each oligonucleotide and therefore the nucleotide sequence at each position in the SST motif facilitates modification of the motif in a defined and controlled manner. The invention also provides pluralities of the SST motifs that are substantially monodisperse with respect to size, shape and/or complexity. Members of the plurality of SST motifs may also be identical to each other with respect to oligonucleotide positioning within each motif, allowing for a plurality of SST motifs to be modified in an identical manner. The plurality of SST motifs thus may be characterized as monodisperse with respect to modification also.

Some SST motifs of the invention are comprised of parallel double helices with double crossovers, crossovers or half crossovers, or some combination thereof. Typically, a plurality of single stranded oligonucleotides anneals to form a double helix in the motif.

Each oligonucleotide in a SST motif may be unique (i.e., it may be present only once per motif) or it may be present once, twice, three times, or even more frequently. The invention contemplates SST motifs having one or more unique oligonucleotides. In some embodiments, at least one oligonucleotide contributing to a double helix is unique. In some embodiments, at least one double helix in the SST motif comprises an oligonucleotide that is unique from all other oligonucleotides in that helix or in the motif as a whole.

The invention also provides the single stranded oligonucleotides used to generate the SST motifs. Different pluralities of single stranded oligonucleotides are provided, with the nature and composition of those pluralities depending on the design, including shape, size and complexity, of the desired SST motif. As explained in greater detail herein, these pluralities typically comprise 2-domain, 4-domain and 6-domain oligonucleotides.

The invention contemplates that the single stranded oligonucleotides and the SST motifs are modular in nature. The methods of the invention allow for variously shaped SST motifs to be made by inclusion and/or exclusion of a subset of known oligonucleotides. The methods also contemplate modular assembly of SST motifs to each other, for example by annealing such motifs to each other based on sequence specificity. In some of these embodiments, the SST motifs that are annealed to each other may share a common shape (e.g., both may be tubes, or both may be lattices). The methods also contemplate composite SST motifs made by linking two or more SST motifs to each other using linkers (e.g., poly T linkers) that may or may not be integral to the SST motif. In these embodiments, SST motifs that are linked to each other may be of the same or of different shape.

The invention also contemplates synthesis of SST motifs that exhibit variations in surface curvature and complexity (e.g., corrugation), twist and flexibility/structural rigidity. In some embodiments, the surface curvature of a SST motif may be controlled by altering the lengths and arrangement of complementary domains of single stranded oligonucleotides used to assembly the motif. In some embodiments, the SST motifs may exhibit a "twisted" geometry, which may be controlled by altering the helical turn geometry (e.g., from 10.5 base pairs per helical turn to 9-13 base pairs per helical turn) and by extending the motifs along their helical axis. In some embodiments, the flexibility of the SST motifs may be controlled by introducing double crossovers to achieve longer distances between adjacent crossovers or by the addition of linkers (e.g., poly T linkers or other specified sequences).

The invention further contemplates synthesis of SST motifs by combining a plurality of known single stranded oligonucleotides in a single vessel and allowing the oligonucleotides to self-assemble, in a predetermined manner, under suitable conditions. Similarly, two or more SST motifs may be combined in a single vessel and allowed to self-assemble in a predetermined manner, under suitable conditions, based on nucleotide sequence complementarity, thereby forming a larger nucleic acid motif.

Thus, in one aspect, the invention provides a SST motif comprising a plurality of annealed oligonucleotides, each oligonucleotide comprising at least two domains, arranged into at least two parallel double helices, wherein at least one double helix comprises a unique domain.

In some embodiments, at least one double helix comprises 2 or more unique domains. In some embodiments, at least 50% of the double helices comprise one or more unique domains. In some embodiments, the motif comprises at least 5, at least 10, or at least 20 parallel double helices.

In another aspect, the invention provides a SST motif comprising a plurality of annealed oligonucleotides, each oligonucleotide comprising at least two domains, arranged into at least two parallel double helices, wherein at least one double helix is unique.

In some embodiments, the motif comprises 2 or more unique double helices. In some embodiments, at least 50% of the double helices are unique. In some embodiments, at least 50% of the double helices comprise one or more unique domains. In some embodiments, the motif comprises at least 5, at least 10, or at least 20 parallel double helices.

In another aspect, the invention provides a SST motif comprising a plurality of annealed oligonucleotides, each oligonucleotide comprising at least two domains, arranged into at least two parallel double helices, wherein at least one oligonucleotide in the motif is unique.

In some embodiments, at least 50% of the oligonucleotides in the motif are unique. In some embodiments, all of the oligonucleotides in the motif are unique. In some embodiments, the motif comprises at least 5, at least 10, or at least 20 parallel double helices.

In another aspect, the invention provides a composition comprising a plurality of SST motifs of any of the foregoing claims, wherein the plurality is at least 50% homogeneous.

In another aspect, the invention provides a method comprising annealing a plurality of single stranded oligonucleotides in a single vessel to form a SST motif, wherein the single stranded oligonucleotides each comprise at least two domains, and wherein at least one single stranded oligonucleotide is present at a molar concentration that is 10-fold lower than the molar concentration of other oligonucleotides in the plurality.

In another aspect, the invention provides a method comprising annealing a plurality of single stranded oligonucleotides in a single vessel to form a SST motif, wherein the single stranded oligonucleotides each comprise at least two domains, and wherein at least one single stranded oligonucleotide is present at a molar concentration that is 100-fold lower than the molar concentration of other oligonucleotides in the plurality.

In some embodiments, annealing occurs through a temperature transition over a period of time. In some embodiments, the temperature transition is a change in temperature from an elevated temperature to about room temperature. In some embodiments, the temperature transition is a change in temperature from about 90° C. to about room temperature. In some embodiments, the annealing occurs over a period of about 12-24 hours.

In another aspect, the invention provides a SST motif prepared by any of the foregoing methods.

In another aspect, the invention provides a composite SST motif comprising at least two SST motifs of any of the foregoing claims, conjugated to each other through a linker.

In some embodiments, the linker comprises nucleic acid elements and non-nucleic acid elements. In some embodiments, the linker comprises a carbon chain. In some embodiments, the linker is a homo-bifunctional linker.

In some embodiments, a first subset of oligonucleotides comprises 2 domains and a second subset of oligonucleotides comprises 4 domains or 6 domains. In some embodiments, the oligonucleotides are 18-104 nucleotides in length. In some embodiments, the single stranded oligonucleotides are DNA oligonucleotides. In some embodiments, the single stranded oligonucleotides are L-DNA oligonucleotides. In some embodiments, the single stranded oligonucleotides are RNA oligonucleotides. In some embodiments, the single stranded oligonucleotides comprise modifications such as but not limited to backbone modifications, sugar modifications and/or base modifications. The single stranded oligonucleotides may be homogeneous or heterogeneous respecting such and other modifications.

In one aspect, the invention provides a SST motif comprising a plurality of unique oligonucleotides, wherein all the oligonucleotides are less than 1 kb in length. In some embodiments, the oligonucleotides are less than 100 bases in length. In some embodiments, some oligonucleotides in the motif are n oligonucleotides in length (where n represents an integer that is a multiple of 9, 9.5, 10, 10.5, 11, 11.5, 12, 12.5, or 13) and some oligonucleotides are n/2 or n2 in length. In some embodiments, some oligonucleotides are about 54, 57, 60, 63, 66, 69, 72, 75 or 78 nucleotides in length (e.g., the 6-domain oligonucleotides), some oligonucleotides are about 36, 38, 40, 42, 44, 46, 48, 50 or 52 nucleotides in length (e.g., the 4-domain oligonucleotides), and some oligonucleotides are about 18, 19, 20, 21, 22, 23, 24, 25 or 26 nucleotides in length (e.g., the 2-domain oligonucleotides).

The invention contemplates SST motifs having a variety of arrangements of oligonucleotides. In some embodiments, the SST motifs comprise oligonucleotides that comprise, as an example, 4 domains, wherein 2 such domains are bound to one domain on a distinct and separate oligonucleotide in the motif. In some embodiments, the 2 domains that bind to a single domain in another oligonucleotide may not be contiguous to each other or linked to each other when bound to the other single domain. In some embodiments, the motifs contain half crossovers, crossovers, double-crossovers or any combination of two or more of the foregoing.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE FIGURES

It is to be understood that the Figures are not necessarily to scale, emphasis instead being placed upon generally illustrating the various concepts discussed herein.

FIGS. 5A-5C show schematics and AFM images of various geometrically-distinct SST motifs.

DETAILED DESCRIPTION OF INVENTION

Figure 1:
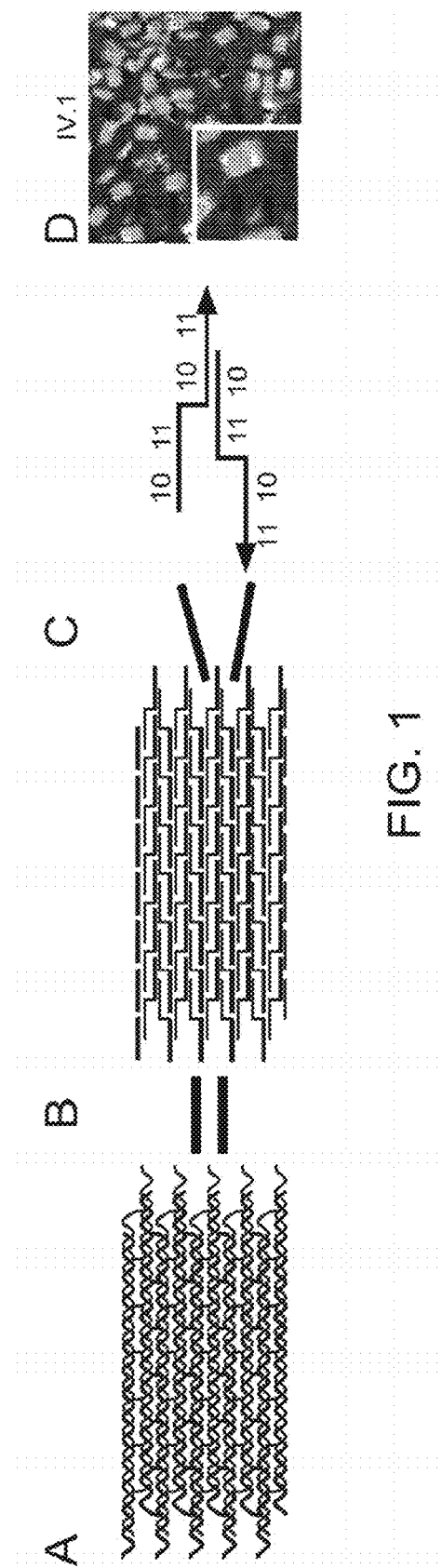
FIGS. 1A-1D show schematics and an atomic force microscopy (AFM) image of a single stranded tile (SST) motif.

The invention relates, in its broadest sense, to methods of synthesizing nucleic acid structures (SST motifs) of predetermined, and thus controlled, shape, size and complexity. The invention is premised, in part, on the unexpected finding that the geometric properties (e.g., curvature, twist and flexibility) of SST motifs can be controlled by adjusting complementary single stranded oligonucleotide length and arrangement, altering interhelical crossover patterns, and/or modifying the SST motifs with linkers of different lengths. Earlier thought in the field was that the "stacking" of DNA helices is one of the reasons why DNA nanostructures can form. Surprisingly, the invention demonstrates that SST motifs of the invention having, for example, linkers of different lengths can also form ordered motifs.

The SST motifs of the invention comprise a plurality of oligonucleotides arranged (via sequence-specific annealing) in a predetermined or known manner. As a result, the position of each oligonucleotide in the motif is known. In this way, the motif may be modified, for example through attachment of linkers (or moieties), at particular positions. This may be accomplished by using a modified oligonucleotide as a starting material or by modifying a particular oligonucleotide after the motif is formed. Therefore, knowing the position of each of the starting oligonucleotides in the resultant SST motif provides addressability to the motif.

The SST motifs of the invention may be made, in some embodiments, through a process of self-assembly of single stranded oligonucleotides. In these self-assembly methods, the single stranded oligonucleotides are combined in a single vessel and allowed to anneal to each other, based on sequence complementarity. In some instances, this annealing process involves placing the oligonucleotides at an elevated temperature and then reducing the temperature gradually in order to favor sequence-specific binding. As used herein, the term "self-assembly" refers to the ability of oligonucleotides (and in some instances SST motifs) to anneal to each other, in a sequence-specific, predicted manner without external control (e.g., by sequential addition of oligonucleotides or SST motifs).

The invention therefore provides, inter alia, compositions comprising the single stranded oligonucleotides of the invention; methods of making SST motifs of various predetermined or known size, shape, complexity (e.g., curved, corrugated, twisted) and modification (e.g., with linkers); SST motifs of various predetermined or known size, shape, complexity and modification; pluralities of SST motifs wherein such pluralities may be substantially monodisperse with respect to size, shape, complexity and modification; composite motifs comprising two or more SST motifs; and methods of making such composite motifs. The invention also provides methods of using the SST motifs and the composite motifs of the invention. These aspects and embodiments of the invention will be described in greater detail herein.

Single Stranded Tile (SST) Motifs:

The SST motifs of the invention are comprised of a plurality of oligonucleotides that are bound to each other in a sequence-specific manner. The oligonucleotides of the invention typically comprise two or more domains. FIGS. 1A and 1B provide schematics of multiple 4-domain (e.g., 10-11-10-11) oligonucleotides annealed together to form a SST motif. FIG. 1C shows two single stranded oligonucleotides (each 10-11-10-11) hybridized by complementary base pairing of a single domain in each oligonucleotide (domain 10). The arrow heads represent the 3' end of the single stranded oligonucleotide. Prior to the annealing process that forms the SST motif, the oligonucleotides are in a single stranded form.

Generally, every domain of an oligonucleotide binds to another domain in another oligonucleotide in the motif. FIGS. 1A and 1B provide schematics of the arrangement and binding interactions between 2- and 4-domain oligonucleotides in a region of a SST motif. The 2-domain oligonucleotides are shown in the bottom and top rows, and the 4-domain oligonucleotides are shown in the intermediate rows. The oligonucleotides may also be arranged such that double-crossovers, crossovers and/or half crossovers occur at different distances including but not limited to every two domains or every four domains, and the like. It should be understood that the invention therefore contemplates various binding arrangements for oligonucleotides within a SST motif.

In some instances, however, certain domains in a SST motif may not bind to another domain in the motif. As an example, in some instances, oligonucleotides having a poly T domain are present in the motif, preferably at borders and in configurations that result in the poly T domains being single stranded.

As another example, domains may be used as handles (or linkers) for annealing to other motifs or to other moieties.

The oligonucleotides within a SST motif arrange themselves to form double helices, in some instances, in a parallel arrangement. These double helices are referred to herein interchangeably as helices. These double helices form as a result of the sequence-specific annealing of a select population of single stranded oligonucleotides to each other. Each double helix in the motif is comprised of a plurality of domains. Those domains bind to complementary domains in other oligonucleotides to form the helix. Adjacent helices are connected to each other by half-crossovers, crossovers or double-crossovers.

The invention provides that a SST motif may be designed prior to synthesis, and its size, shape, complexity and modification may be prescribed and controlled by using certain select oligonucleotides in the synthesis process.

It should be understood that the internal oligonucleotides contribute to the desired shape of the motif, and the boundary oligonucleotides prevent unwanted aggregation of motifs to each other.

The assembled SST motifs may exhibit a variety of geometric properties. For example, FIG. 2 schematizes a sampling of the geometric properties contemplated herein, including local curvature, corrugation and twist. The SST motifs of the invention may also be modified with, and joined together by, poly T linkers (or other specified sequence linkers) of different lengths. It is to be understood that multiple different single stranded oligonucleotide types (e.g., different complementary domain lengths, different inter-helical crossover patterns) can be combined within the same SST motif to achieve variation in SST motif geometry, complexity and flexibility.

In some embodiments, the SST motifs are designed to self-assemble into structures with a size of about 5 helices (H) to about 30 helices (10H-25H) by 10 helical turns (T) to about 40 helical turns (10T-40T). For example, a SST motif may have 5, 6, 7, 8, 9, 10, 11, 12, 13, 14, 15, 16, 17, 18, 19, 20, 21, 22, 23, 24, 25, 26, 26, 28, 29 or 30 helices and 10, 11, 13, 14, 15, 16, 17, 18, 19, 20, 21, 22, 23, 24, 25, 26, 26, 28, 29, 30, 31, 32, 33, 34, 35, 36, 37, 38, 39 or 40 helical turns. Thus, in some embodiments, the SST motifs may have a size of 10H×10T, 10H×11T or 10H×12T. In other embodiments, the SST motifs may have a size of or 24H×28T, 24H×29T or 24H×30T.

It should also be understood that the oligonucleotides of the invention may be designed manually or by computer means based on the teachings provided herein.

As an example, oligonucleotides may be constructed using a process that minimizes the sequence symmetry or that populates the SST motifs with completely random sequences. Either process may employ software such as Uniquimer. For the sequence minimization based design, there are several criteria for sequence generation. 1) Nucleotides (i.e. A, C, G, T) are randomly generated one-by-one. 2) Complementary nucleotides to those generated are matched following the base pairing rule: A to T and vice versa, C to G and vice versa. 3) No repeating segment beyond a certain length (8 nt or 9 nt) is permitted. When such repeating segments emerge during design, the most recently generated nucleotides will be mutated until the repeating segment requirement is satisfied. 4) No four consecutive A, C, G or T bases are allowed. 5) Pre-specified nucleotides at the single stranded linkage points (e.g., T and G for the $21^{st}$ and $22^{nd}$ nucleotides, respectively, for most of the strands) are used to avoid sliding bases around the linkage points. In the design using completely random sequences, however, restrictions in steps 3 to 5 are not applied.

Some or all of the oligonucleotides may be manually designed.

In some embodiments, at least one domain in a SST motif may be unique, intending that the domain appears only once in that motif. A motif may be comprised of one or more unique domains, including 1, 2, 3, 4, 5, 6, 7, 8, 9, 10, 20, 30, 40, 50, 60, 70, 80, 90, 100, 200, 300, 400, 500, 600, 700, 800, 900, 1000 or more unique domains. In some embodiments, at least 10%, 20%, 30%, 40%, 50%, 60%, 70%, 80%, 80% or 90% of the domains in the motif are unique. As an example, a SST motif may comprise a first plurality of domains each of which appears only once in the motif and these unique domains may present 75% of the total domains in the motif, and a second plurality of domains each of which appears more than once in the motif and these repeating domains may represent 25% of the total domains in the motif. It will be apparent that other percentages are also possible. In some embodiments, every domain in a SST motif is unique. Every domain in a composite motif (i.e., a motif comprising two or more SST motifs linked to each other with a linker) may or may not be unique.

In some embodiments, at least one domain in a double helix in a motif may be unique, intending that the domain appears only once in that double helix. The domain may be present in other helices within the same motif, and so it may not be unique in the context of the entire SST motif. There may be 1, 2, 3, 4, 5, 6, 7, 8, 9, 10 or more domains in a helix that are unique in the context of that helix. The unique domains in a helix may represent at least 10%, 20%, 30%, 40%, 50%, 60%, 70%, 80%, 80%, 90% or 100% of the domains in that helix. The unique domains in a helix may be located at or near the ends of the motif. The unique domains in a helix may be contiguous to each other or they may be spread apart from each other. They may be separated from each other by repeating domains (i.e., domains that appear more than once in a helix).

The motifs may comprise one or more helices having unique domains. This type of helix may represent at least 10%, 20%, 30%, 40%, 50%, 60%, 70%, 80%, 90% or 100% of the helices present in the motif. If more than one of this helix type is present in the motif, they may be adjacent to each other or they may be separated by other helices, including helices that do not contain unique domains. As an example, helices having unique domains may alternate in the motif with helices lacking unique domains.

Thus, in some embodiments, the SST motif may comprise two or more helices, each having one or more unique domains, wherein the domain is unique in the context of an individual helix itself and possibly unique within the context of the motif as a whole. The unique domain(s) in an individual helix may be present in other helices in the motif. The unique domain(s) in an individual helix may be the unique domain(s) in other helices in the SST motif.

In some embodiments, one or more helices in the motif each may be comprised entirely of unique domains, intending that each of those domains is present only once per helix or is present only once per motif.

Thus, in some embodiments, the SST motifs of the invention comprise at least one unique double helix. A unique double helix is a helix having a domain composition that is different from any other helix in the motif. The unique double helix would therefore also have a nucleotide sequence that is different from any other helix in the motif.

In some embodiments, the SST motifs of the invention may be designed such that they comprise one region that is comprised of unique domains and another region that is comprised of non-unique domains or repeating domains.

The SST motifs are formed, at least in part, by annealing a plurality of known oligonucleotides in a single vessel. The methods provide that, starting with a known pool of oligonucleotides that can be used to generate a lattice of a certain size, select oligonucleotides may be excluded from the pool in order to form different shaped and/or sized motifs.

Figure 5A:
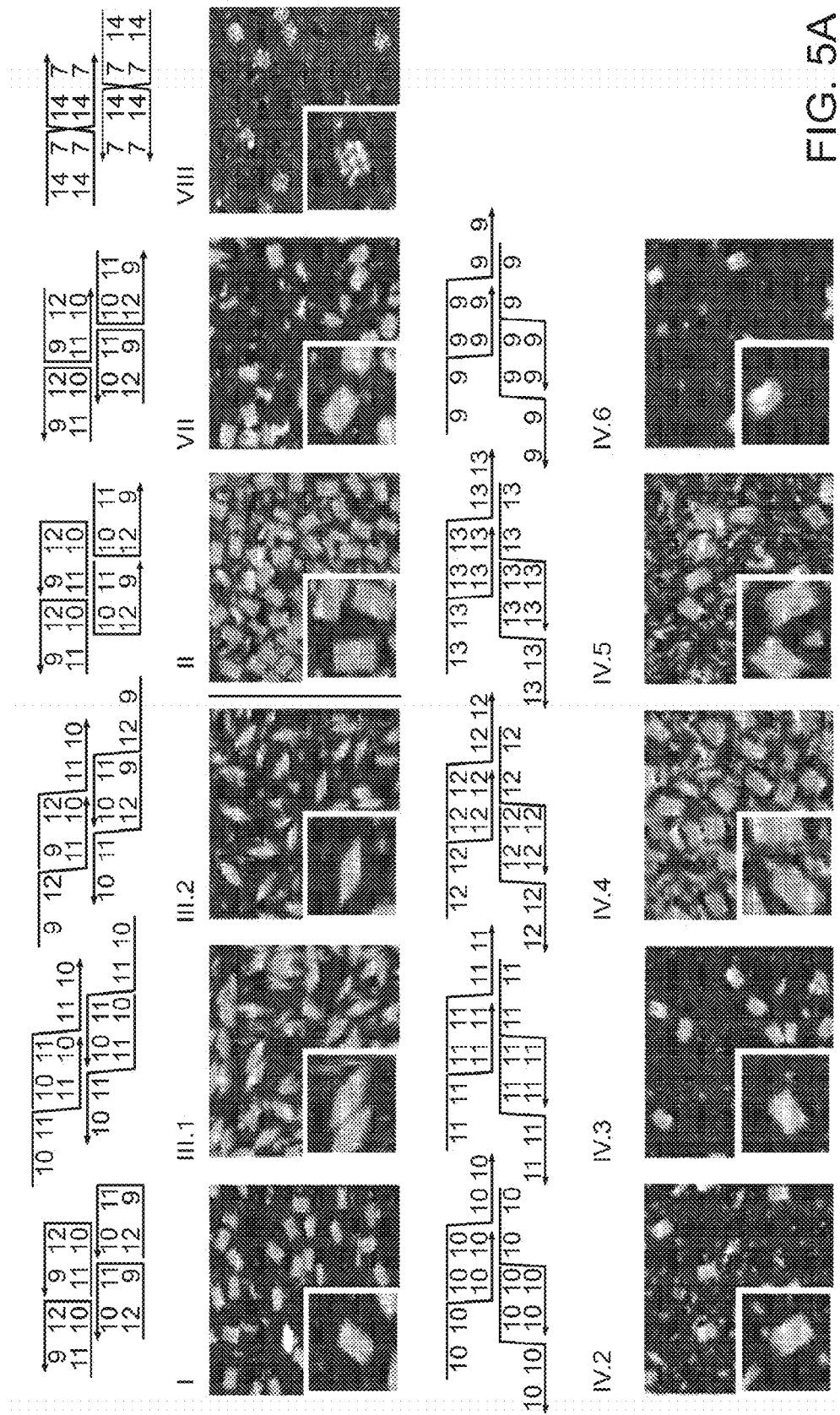
Figure 5B:
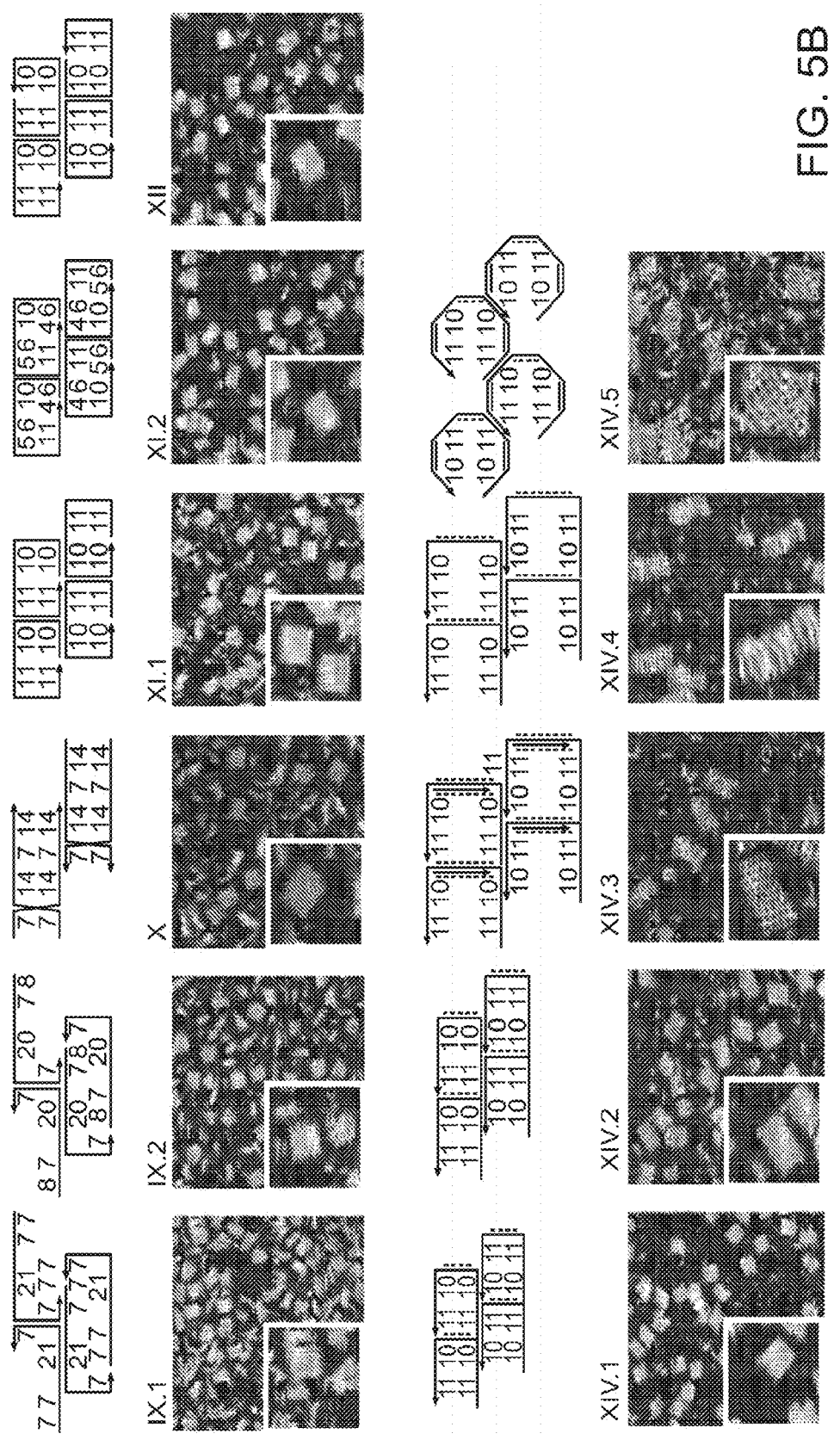
Figure 5C:
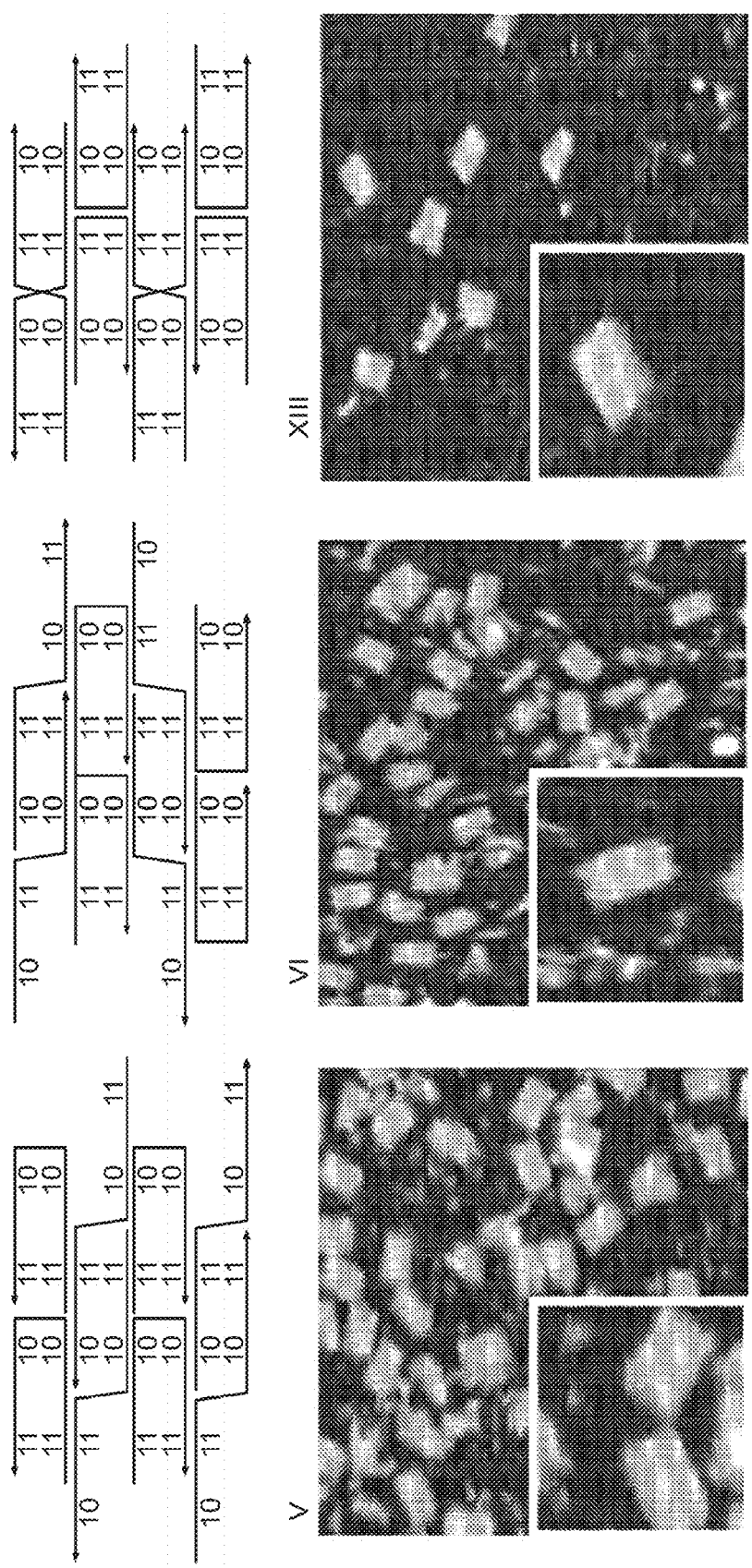
Figure 6A:
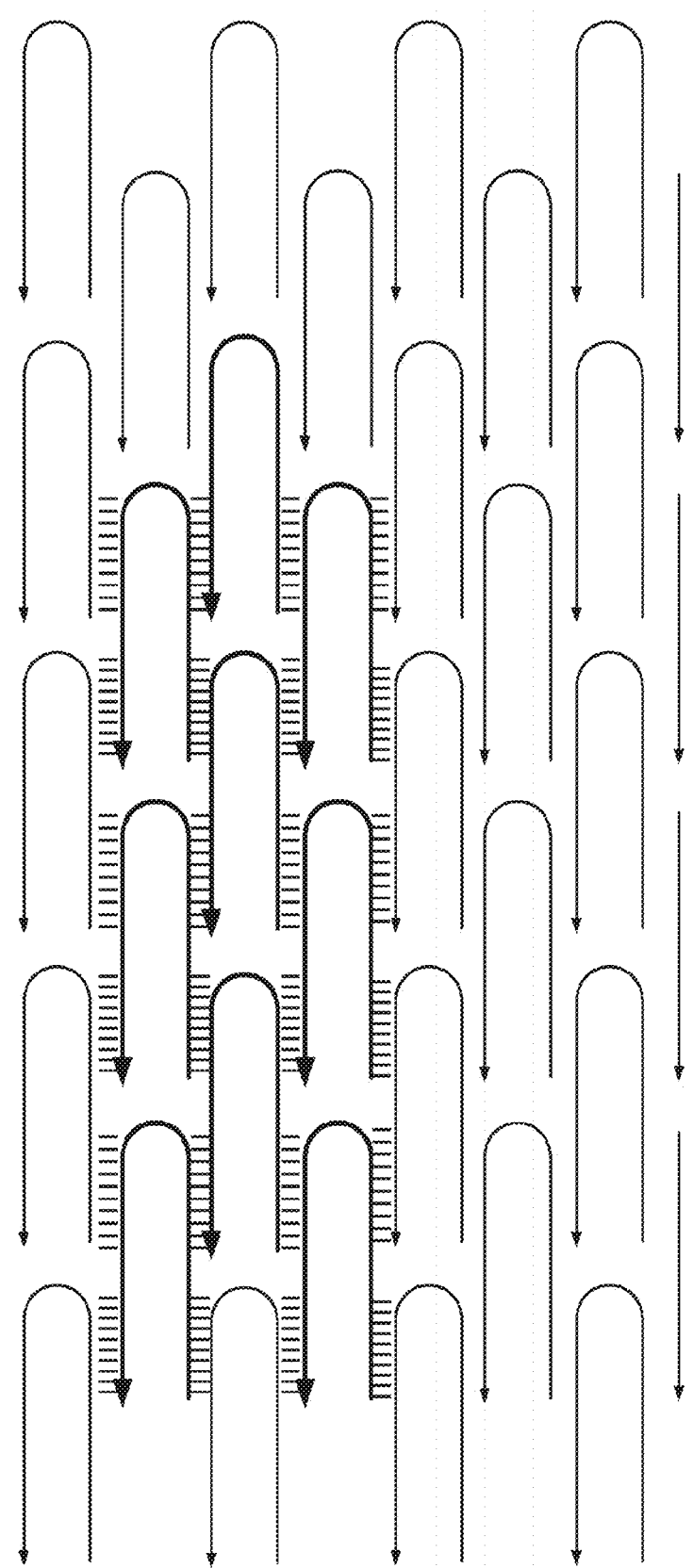
FIG. 6A is a schematic of a region of a SST motif showing 4-domain single stranded oligonucleotides (represented in this Figure by "U" shaped structures) and 2-domain single stranded oligonucleotides (represented by linear structures at the bottom). Illustrated are the inter-domain, inter-oligo-nucleotide bonds, and half crossovers between helices. The half crossovers are also illustrated and are comprised of phosphate backbone moieties. The half-crossovers typically do not comprise a nucleotide and thus do not contribute to sequence-specific binding and do not dictate the location or position of an oligonucleotide in the structure. For illustration purposes, nine of the 4-domain oligonucleotides are shown bonded to each other and/or other oligonucleotides. In this illustration, all nine have a unique sequence relative to each other.
Figure 6B:
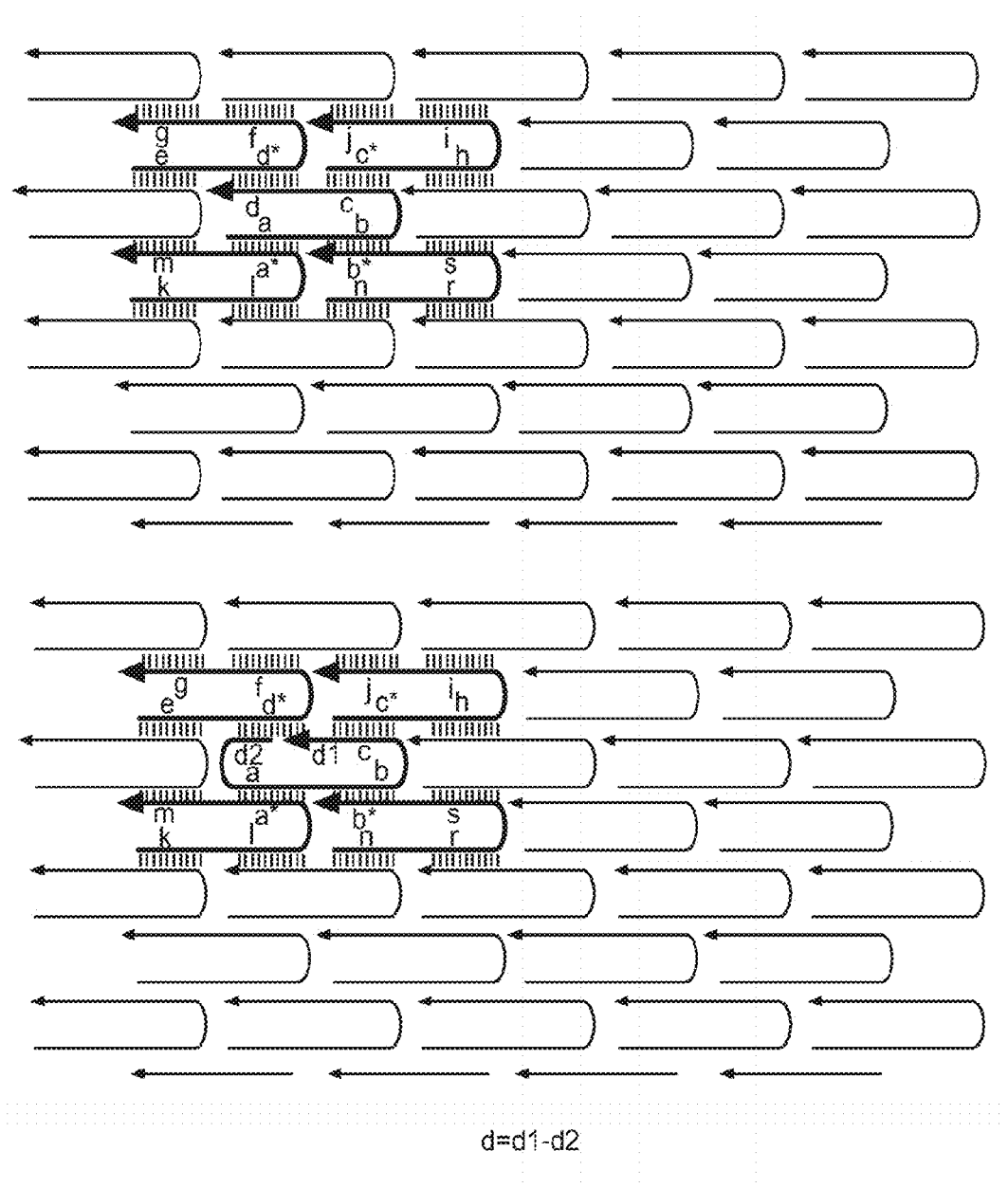
FIG. 6B is a schematic of regions of two nucleic acid structures showing the arrangement of 2- and 4-domain single stranded oligonucleotides. In the top schematic, each 4-domain oligonucleotide is configured in a "U" shape and provides only a single half crossover between the two double helices to which it contributes. In the bottom schematic, one of the 4-domain oligonucleotides contributes two half crossovers between the double helices to which it contributes. The structure therefore contains a crossover and multiple half crossovers. The same oligonucleotide may be characterized as having a domain order of 5' d2-a-b-c-d1 3', wherein domains d1 and d2 bind to domain d* in forming the double helix. The domains are labeled with different identifiers to indicate unique sequences relative to each other.
Figure 7:
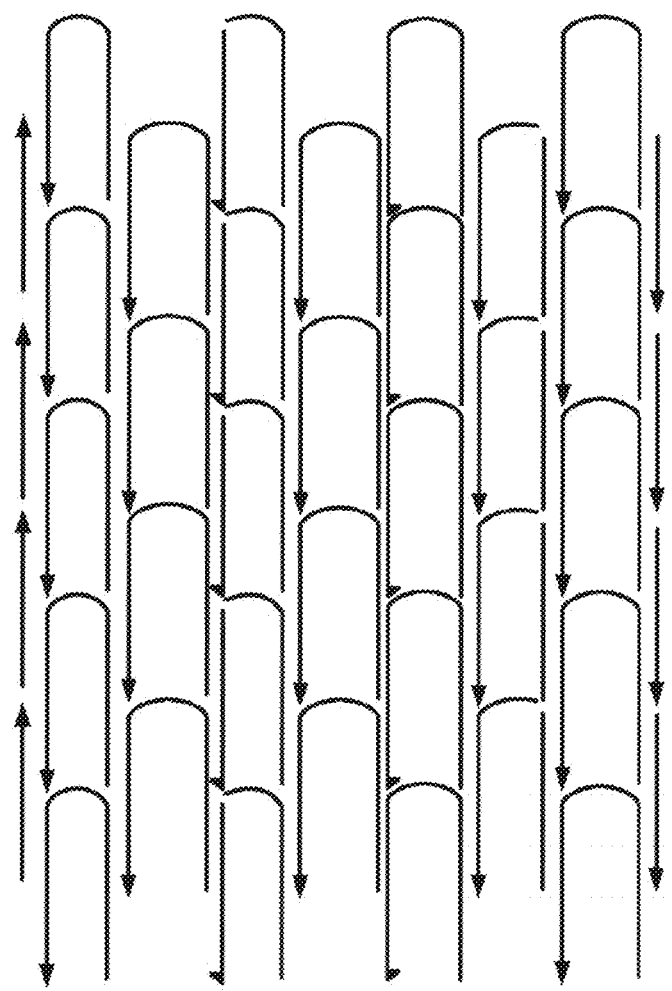
FIG. 7 is a schematic of a four parallel double helix lattice made up of 12 distinct oligonucleotides (left) and an eight parallel double helix square made up of 40 distinct oligonucleotides (right).
Figure 7:
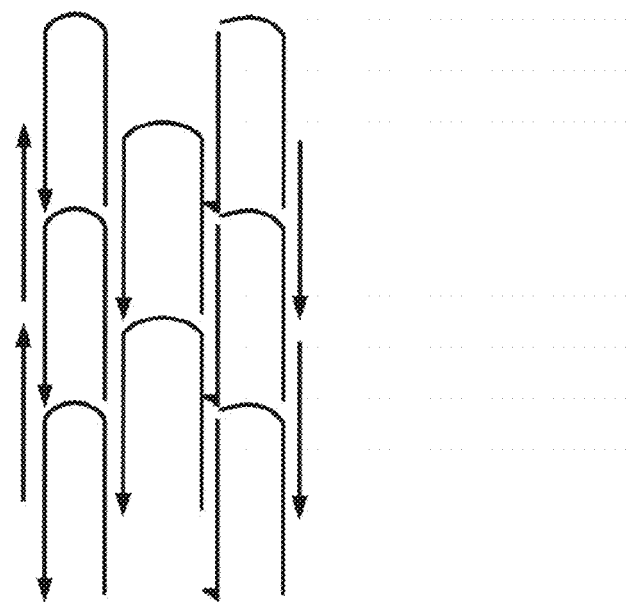

A variety of SST motifs that may be made using these methods are shown in FIG. 5. In some embodiments, symmetric SST motifs may be synthesized using U-shaped single stranded oligonucleotides with alternating orientations with (motif VII) or between (motif II) rows of a structure. In some embodiments, the SST motifs exhibiting a twisted design (motifs IV.2-IV.6) may be synthesized by altering the canonical 10.5 bp per helical turn geometry, for example, to 9-13 bp per helical turn and extending the SST motifs along the helical axis. For example, the single stranded oligonucleotides used to assemble motifs IV.2-IV.6 were extended from 36 bp (motif IV.6) to 40 bp (motif IV.2) to 44 bp (motif IV.3) to 48 bp (motif IV.4) to 52 bp (motif IV.5), thereby altering the number of base pairs per helical turn and the degree of twist in the motif. In some embodiments, the structural rigidity of the SST motifs are altered (e.g., made more flexible) by introducing double crossovers to obtain longer distances between adjacent crossovers (motifs IX.1, IX.2 and X) and/or by adding linkers (e.g., poly-T linkers or other specified sequences) between some (motifs XIV.1-XIV.4) or all (motif XIV.5) domains.

In some embodiments, "hybrid" SST motifs may be created by combining several different motifs or by combining several different types (e.g., of different domain length and number) of single stranded oligonucleotides as shown, for example, in FIG. 5, motifs V, VI and XIII. FIG. 5, motif V shows a SST motif assembled from the combination of U-shaped oligonucleotides having a domain length combination of 11-10-10-11, S-shaped oligonucleotides having a domain length combination of 11-10-11-10, and S-shaped oligonucleotides having a domain length combination of 10-11-10-11. FIG. 5, motif VI shows a SST motif assembled from the combination of U-shaped oligonucleotides having a domain length combination of 11-10-10-11, U-shaped oligonucleotides having a domain length combination of 10-11-11-10, S-shaped oligonucleotides having a domain length combination of 10-11-10-11, S-shaped oligonucleotides having a domain length combination of 10-11-11-10, and S-shaped oligonucleotides having a domain length combination of 11-10-11-10. Thus, in some embodiments, a SST motif may comprises 1, 2, 3, 4, 5, 6, 7, 8, 9 or 10 different types of single stranded oligonucleotides. It is to be understood that the number of different types of single stranded oligonucleotides is not limited.

Further, in some embodiments, a SST motif may comprise different types of single stranded oliogonucleotides as well as half crossovers, crossovers, double crossovers or a combination of any two or more half crossovers, crossovers and double crossovers. The invention contemplates combinations of any of the embodiments described herein provided that the combination does not adversely affect the stability of the SST motif, unless intended by the end user.

In some embodiments, an end user designs a SST motif, such as for example a lattice having a particular length and a width dimension, with knowledge of the particular oligonucleotide present at each position in the motif. In effect, the end user has a physical map that denotes the precise location of each oligonucleotide within the SST motif. Knowledge of the identity of each oligonucleotide at each location in the map (and thus in the SST motif) allows the end user to engineer particular patterns or shapes using a particular SST motif as a starting point. Such engineering can occur by excluding one or more known oligonucleotides from the mixture of oligonucleotides combined to form the SST motif and/or including additional known oligonucleotides.

Thus, as an example and as demonstrated herein, an end user may design a two dimensional lattice having a particular length and width, and comprised of a plurality of unique oligonucleotides. The end user knows the identity of the oligonucleotide at each position in the lattice. In addition to being able to synthesize the lattice itself, the end user is also able to design and synthesize one or more other SST motifs using the lattice as a starting point. As demonstrated herein, SST motifs of various shapes and complexities be synthesized by excluding one and usually more oligonucleotides from the pool that would be used to make the entire lattice. These shapes include heart shapes, chevrons, and triangles, as well as lattices or other motifs with internal openings or holes. The SST motifs may also exhibit various geometric properties such as, for example, local curvature, corrugation, twist and flexibility.

The invention therefore provides a methodology for synthesizing a number of different SST motifs without having to design each motif de novo. Rather, starting with an initial SST motif, such as a lattice, a variety of other SST motifs may be formed simply by excluding preselected oligonucleotides and/or including preselected oligonucleotides. In this way, the end user uses the single stranded oligonucleotides in a modular manner, including or excluding members of the plurality depending upon the ultimate shape and size of SST motif desired. The interactions between oligonucleotide members of the plurality are not expected to change appreciably and therefore it is not necessary for an end user to design, essentially from scratch, every new SST motif. Instead, the end user prepares stocks of each oligonucleotide and combines various stocks together, at relative concentrations corresponding to their relative frequency in the motif and in a single vessel, in order to form a SST motif of desired shape, size and complexity.

The selection and arrangement of single stranded oligonucleotides in a SST motif of desired shape and size can be done manually or by computer algorithm. An example of such a computer algorithm is Uniquimer, which is openly available to the public.

The size of the SST motifs of the invention may be controlled during the annealing process. This size control is achieved by designing motifs having one or more unique domains, or one or more unique helices and thus using select populations of oligonucleotides in the annealing process. The size of the SST motif thus is typically also predetermined.

The size of a SST motif may be represented by distance of one, two or three of its dimensions. Such dimensions may each independently be nanometers or micrometers in length, or longer. As an example, the motif may comprise one or two dimensions each having a length in the range of 5-100 nanometers, 5-500 nanometers, 5-1000 nanometers, including 10-100 nanometers, 10-500 nanometers, or 10-1000 nanometers. In some embodiments, they may have one or more dimensions of about 10, 20, 30, 40, 50, 60, 70, 80, 90, 100, 110, 120, 130, 140, 150, 160, 170, 180, 190, 200, 300, 400, 500, 600, 700, 800, 900 nm or more. In some embodiment, the motif is about 3 nm by 7 nm or about 4 nm by 7 nm. In some embodiments, the motif is 60 nm by 100 nm.

The size of the SST motif may also be presented by the number of double helices as well as the length of those double helices. The length of a double helix may be expressed as the number of helical turns in the helix. It is to be understood that the invention contemplates making motifs that are in the nanometer and micrometer scale, and larger.

The size of the SST motif may also be presented as the number of 4-domain oligonucleotides it comprises. The range may be from 1 to more than 1000. The number of single stranded oligonucleotides contributing to a SST motif may vary depending on the size of motif desired and/or the degree of modification and/or complexity desired. Some of the exemplified SST motifs comprise at least 4-fold more distinct molecular components as compared to previously reported one-pot annealing motifs.

The size of the SST motif may also be presented as the number of nucleotides it comprises. Some of the exemplified motifs comprise at least 3-fold more nucleotides than a typical DNA origami motif (i.e., a motif comprised of a single scaffold strand and a plurality of staple strands).

The SST motifs of the invention may take any shape or form. In some embodiments, the SST motifs are curved or corrugated. In some embodiments, the SST motifs are twisted. Importantly, using the methodology of the invention, it is possible to predetermine and thus predesign the shape, form and size of the SST motif with precise control based on knowledge of the identity (and thus sequence) of oligonucleotides at every location in the motif.

As discussed herein, SST motifs may be synthesized by combining and annealing a plurality of single stranded oligonucleotides in a single annealing reaction to yield a SST motif of desired shape, size, complexity and modification. The invention also contemplates synthesis of SST motifs by annealing separate smaller SST motifs to each other, in a modular manner. This approach has been used to fuse together lattice-shaped motifs to each other and tube-shaped motifs to each other. Such fusion may also occur without the need to purify the motifs from their initial synthesis annealing reaction solution. Thus, whether purified or not, the motifs may be combined and annealed.

In some embodiments, the SST motifs are annealed by subjecting them to an elevated temperature and then a slow cooling process. The elevated temperature may be about 50° C., about 45° C. or about 40° C., and the cooling process is intended to cool the solution to about room temperature (e.g., about 25° C.). The cooling period may be several hours including 2, 3, 4, 5, 6, 7, 8, 9 or 10 hours or more. Alternatively, the SST motifs may be combined and allowed to anneal at a single temperature, including for example room temperature for the same length of time.

In other embodiments, the invention contemplates staggered or sequential addition (and annealing) of motifs, as compared to simultaneous mixture and annealing of all motifs. Sequential addition may be particularly useful in the synthesis of more complex motifs. In some instances, these and other annealing methods can be carried out either in a static environment or under flow. A flow environment allows non-annealed oligonucleotides or nucleic motifs to be removed prior to the addition of subsequent components.

The invention also provides pluralities of SST motifs. As used herein, the term plurality intends more than one and may be used interchangeably with the term population. Such pluralities may comprise 10, 50, 100, 500, 1000 or more motifs. Such pluralities may have varying degrees of homogeneity intending that a percentage of the SST motifs in the plurality are identical to each other with respect to size, shape, complexity and/or modification. The plurality of motifs therefore may be at least 20%, 30%, 40%, 50%, 60%, 70%, 80%, 90%, or 100% homogeneous in motifs having a certain characteristic. As an example, a plurality of lattice shaped motifs may be at least 50% homogeneous intending that at least 50% of the motifs in that plurality are lattice shaped.

Such pluralities may be monodisperse intending that their members may be identical in terms of one or more characteristics including size, shape, complexity and/or modification. The pluralities may be monodisperse for all of these characteristics. In some embodiments, the pluralities are substantially monodisperse. Substantially monodisperse refers to pluralities in which at least 50%, 60%, 70%, 80%, 90%, or more of the motifs are of about the same shape, size, complexity and/or have the same modification. In some embodiments, at least 10%, 20%, 30%, 40% or more of the motifs are of about the same shape, size, complexity and/or have the same modification.

The degree of homogeneity (and conversely heterogeneity) in a plurality may be determined using a number of techniques, including but not limited to AFM or TEM, and gel electrophoresis. These techniques have been used to determine the degree of homogeneity in prepared populations of motifs, as discussed in the Examples. Importantly, it has been found that the annealing methods provided herein reproducibly yield populations having a predominant SST motif species. Moreover, that predominant species appears identical to the species that was intended using the design and mapping approach of the invention.

In some instances, once a SST motif is formed, there may still be domains that are single stranded. These may exist, for example, at the borders. It has been found in accordance with the invention that the nature of such domains can impact the efficiency and yield of the annealing process. More specifically, if these single stranded regions are of a mixed nucleotide sequence, then the motifs are more likely to agglomerate, and yield is reduced. Such agglomeration can be reduced by manipulating the nucleotide sequence of these single stranded regions. Specifically, single stranded regions that are poly T in sequence are less likely to cause agglomeration, resulting in better yields of motifs. Poly A and poly C sequences may also be used. In some embodiments, therefore, certain single stranded domains may be present in a motif and such domains may be identical to each other in sequence.

In some embodiments, border regions may be comprised of a mixture of poly T domains and other domains of mixed sequence, provided that the motifs do not agglomerate substantially. In these embodiments, the mixed sequence domains may be used to anneal two or more motifs to each other. The number of such domains may be 6, 8, 10 or more.

The SST motifs of the invention may be modified during synthesis or post-synthesis. They may be modified during synthesis by using oligonucleotides that are modified. For example, one or more oligonucleotides used to generate a SST motif may be conjugated to a moiety of interest. Modified oligonucleotides may be used to generate the SST motifs of the invention provided such modifications do not interfere with the ability of the oligonucleotides to bind to other oligonucleotides as required in order to form the desired motif. Additionally or alternatively, the SST motif may be modified post-synthesis.

Any modification is contemplated provided it does not interfere with the annealing of oligonucleotides to each other and it does not render the SST motif less stable, unless that is otherwise intended by the modification. Modification may be, but is not limited to, chemical or enzymatic in nature. Modification may involve the use of nucleic acid conjugated moieties. The moieties may be, without limitation, metallic, organic and inorganic in nature. The moieties may be conjugated to nucleic acids that are able to recognize and bind to oligonucleotides in the motif. Such nucleic acids may be triplex forming oligonucleotides, as an example. In some instances, one or more non-nucleic acid moieties may be attached, permanently or transiently, covalently or non-covalently, to the SST motifs. The invention contemplates that unique and/or non-unique oligonucleotides may be modified. The oligonucleotides in a SST motif may themselves be conjugated to one or more domains that do not contribute to the motif but rather are used to bind moieties to the motif. It is to be understood that, because the location of each oligonucleotide and each domain in the motif can be predetermined, the location of each modification to the ultimate resulting SST motif can also be predetermined. In other words, knowledge of the location of each oligonucleotide in the motif facilitates the addressability of the motif.

Single Stranded Oligonucleotides:

The SST motifs of the invention are designed and made using a plurality of single stranded oligonucleotides that anneal to each other in a sequence-specific manner. The oligonucleotides may be characterized by their length, their sequence, and their domain composition. The number and sequence of their domains governs the binding activity and location of each oligonucleotide. Their domain number typically governs the number of oligonucleotides each oligonucleotide will bind to in a motif.

In some embodiments, the oligonucleotides used to make a motif comprise an even number of domains. Each oligonucleotide typically comprises at least two domains. In some embodiments, oligonucleotides used to make a motif may be 2- and 4-domain oligonucleotides. It is also possible to form motifs using other combinations of oligonucleotides including without limitation 2- and 6-domain oligonucleotides, 3- and 6-domain oligonucleotides, 2- and 8-domain oligonucleotides, 4- and 8-domain oligonucleotides, and the like.

A domain, as used herein, refers to a nucleotide sequence (i.e., a number of contiguous nucleotides or nucleotide analogs having the ability to bind in a sequence-specific manner to their complements). The domains in a plurality of oligonucleotides or in a SST motif are designed such that they anneal to domain in another oligonucleotide. The collective complementarity of all domains of an oligonucleotide facilitates the self-assembly of such oligonucleotides to form SST motifs.

The domain length may vary. For example, a single domain may have a length of 1, 2, 3, 4, 5, 6, 7, 8, 9, 10, 11, 12, 13, 14, 15, 16, 17, 18, 19, 20, 21, 22, 23, 24, 25 or 26 nucleotides. The combined length of two contiguous domains that contribute to the same helix will typically have a length that is h×k where h represents the number of monomer units (such as for example nucleotides) required to make a full helical turn and k represents any integer of 1 or greater. As an example, for B form DNA there are typically 10.5 nucleotides per helical turn, while for RNA there are 11 nucleotides per helical turn. Thus, for domains that are B form DNA in nature, the combined length of two contiguous domains that contribute to the same helix can be represented as 10.5*k (rounding off to the nearest integer) where k represents an integer of 1 or greater, wherein * denotes a multiplication sign.

The invention also contemplates altering the canonical 10.5 bp helical turn geometry from about 9 bp to about 13 bp. In this way, the "twist" of a SST motif can be adjusted (see, e.g., FIG. 1). Thus, in some embodiments, the combined length of two contiguous domains that contribute to the same helix can be represented as 9*k, 9.5*k, 10*k, 10.5*k, 11*k, 11.5*k, 12*k, 12.5*k or 13*k.

In situations where two contiguous domains from the same oligonucleotide are contributing to the same helix, the lengths of the two domains may be interrelated. Assume that the combined length of two such domains is x where x is h*k as defined above (where h is 10.5). In that case, one domain has a length of y and the other domain has a length of x−y, provided that y is 1 or greater. As an example, in one embodiment, each of a first and a second DNA domain may range in length from 1-20 nucleotides provided that the combined length of the two domains is 21 nucleotides.

In some embodiments, two contiguous domains that contribute to the same helix may have a combined length of about 18+/−2, 19+/−2, 20+/−2, 21+/−2, 22+/−2, 23+/−2, 24+/−2, 25+/−2 or 26+/−2 nucleotides in length, or any integral multiple of 9, 9.5, 10, 10.5, 11, 11.5, 12, 12.5 or 13 nucleotides. Two contiguous domains may have a total combined length of, for example, 18, 19, 20, 21, 22, 23, 24, 25, 26, 27 or 28 nucleotides. A 2-domain oligonucleotide may have a length of, for example, 18+/−2, 19+/−2, 20+/−2, 21+/−2, 22+/−2, 23+/−2, 24+/−2, 25+/−2 or 26+/−2 nucleotides. A 4-domain oligonucleotide may have a length of, for example, 36+/−2, 38+/−2, 40+/−2, 42+/−2, 44+/−2, 46+/−2, 48+/−2, 50+/−2 or 52+/−2 nucleotides.

Thus in general, two consecutive domains participating in the same duplex with a total length x=h*k as defined above, x can be h*k+/−a, where a=0, 1, 2, . . . , y, where y=(h/2)*k (rounding to the nearest integer). For example, in one embodiment, h=11 (in the case of RNA), k=1, and y=6. Hence, x can be 11+/−0, 1, 2, 3, 4, 5, or 6. As another example, for h=10.5 (in the case of B form DNA), k=2, y=10. Hence x can be 21+/−1, 2, 3, 4, 5, 6, 7, 8, 9, or 10.

In some embodiments, a domain has a length of 6, 7, 8, 9, 10, 11, 12, 13 or 14 nucleotides, two contiguous domains have a length of 12, 13, 14, 15, 16, 16, 18, 19, 20, 21, 22, 23, 24, 25, 26, 27 or 28 nucleotides, and a 4-domain oligonucleotide has a length of 24, 26, 28, 30, 32, 34, 36, 38, 40, 42, 44, 46, 48, 50, 52, 54 or 56 nucleotides. It is to be understood that the invention contemplates oligonucleotides having two contiguous domains (both contributing to a single helix) that have a length that is a multiple of 12, 13, 14, 15, 16, 16, 18, 19, 20, 21, 22, 23, 24, 25, 26, 27 or 28 nucleotides.

Domain length combinations such as 10-11-11-10, 11-10-10-11, 11-10-11-10, and 10-11-10-11, where the first number represents the length of the first domain, the second number represents the length of the second domain, the third number presents the length of the third domain, and the fourth number represents the length of the fourth domain, and where the four domains are arranged as in FIG. 1C, are contemplated by the invention.

In some embodiments, in a given synthesis method or resultant motif, oligonucleotides having the same number of domains will also have the same length. As an example, in one embodiment, all 4-domain oligonucleotides may be the same length and all 2-domain oligonucleotides may be the same length (but that length will be different from that of the 4-domain oligonucleotides). More specifically, some embodiments may use 4-domain oligonucleotides that are one length (e.g., n nucleotides) and 2-domain oligonucleotides that are half that length (e.g., n/2 nucleotides).

In some embodiments, in a given synthesis method or resultant motif, oligonucleotides having the same number of domains will also have different lengths. Exemplary embodiments are presented in FIG. 5. In some embodiments, 4-domain oligonucleotides may have a domain length combination of a-a-a-a, a-a-a-b, a-a-b-b, a-b-c-c or a-b-c-d, where each letter (a, c, b and d) represents a different integer of nucleotides and the combination of integers in a given oligonucleotide add up to 36, 38, 40, 42, 44, 46, 48, 50 or 52. For example, a 4-domain oligonucleotide may have a domain length combination of 9-12-10-11, 10-11-11-10, 14-7-7-14, 10-10-10-10, 7-21-7-7, 7-20-7-8, 14-7-7-14, as exemplified in FIG. 5. As discussed above, the invention also contemplates single stranded oligonucleotides with more than 4 domains. In some embodiments, 6-domain oligonucleotide may have a domain length combination of a-a-a-a-a-a, a-a-a-a-a-b, a-a-a-a-b-c, a-a-a-b-c-d, a-a-b-c-d-e, a-b-c-d-e-f, or a variation thereof. For example, 6-domain oligonucleotides having a domain length combination of 6-11-6-4-10-5 or 6-10-6-5-11-4 are shown in FIG. 5 (motif XI.2). Other domain length combinations may be used in accordance with the invention.

The "internal" oligonucleotides represent the monomer units for the motifs of the invention. As a stand-alone monomer, the oligonucleotide (e.g., 4-domain or 6-domain oligonucleotide) has no well-defined motif. However, upon interaction with neighboring 2- and/or 4- and/or 6-domain oligonucleotides, it folds into a tile-like shape. This is contrasted with previous tile monomers which, as stand-alones, fold into multistranded motifs having a defined, structurally rigid (or semi-rigid) body and several sticky ends. The tile-like shape may be, without limitation, a U-shape (e.g., FIG. 5, motif I), S-shape (e.g., FIG. 5, motif III.1), box-shaped (e.g., FIG. 5, motifs XI.1, XIV.2, XIV.4), hook-shaped (e.g., FIG. 5, motif IV.2) or octagonal-shaped (e.g., FIG. 5, motif XIV.5).

The invention contemplates SST motifs comprising any number of single stranded oligonucleotides. As an example, the SST motifs may comprise as few as 4 and as many as 1000 (or more) oligonucleotides, without limitation. Similarly, pluralities of oligonucleotides used to generate SST motifs may comprise as few as 4 different types of oligonucleotides (as defined by nucleotide sequence) and as many as 1000 (or more) different oligonucleotide species (as defined by nucleotide sequence), without limitation. Thus, depending on the embodiment, the SST motif may comprise 4, 5, 6, 7, 8, 9, 10, 15, 10, 25, 50, 75, 100, 150, 200, 250, 300, 350, 400, 450, 500, 600, 700, 800, 900, 1000, 1100, 1200, 1300, 1400, 1500 or more oligonucleotides. Similarly, depending on the embodiment, a plurality of oligonucleotides used to generate SST motifs may comprise 4, 5, 6, 7, 8, 9, 10, 15, 10, 25, 50, 75, 100, 150, 200, 250, 300, 350, 400, 450, 500, 600, 700, 800, 900, 1000, 1100, 1200, 1300, 1400, 1500, or more different oligonucleotides.

Oligonucleotides, in the context of the invention, include DNA such as D-form DNA and L-form DNA and RNA, as well as various modifications thereof. Modifications include base modifications, sugar modifications, and backbone modifications. Non-limiting examples of these are provided below.

Non-limiting examples of DNA variants that may be used in the invention are L-DNA (the backbone enantiomer of DNA, known in the literature), peptide nucleic acids (PNA) bisPNA clamp, a pseudocomplementary PNA, a locked nucleic acid (LNA), or co-nucleic acids of the above such as DNA-LNA co-nucleic acids. It is to be understood that the oligonucleotides used in products and methods of the invention may be homogeneous or heterogeneous in nature. As an example, they may be completely DNA in nature or they may be comprised of DNA and non-DNA (e.g., LNA) monomers or sequences. Thus, any combination of nucleic acid elements may be used. The oligonucleotide modification may render the oligonucleotide more stable and/or less susceptible to degradation under certain conditions. For example, in some instances, the oligonucleotides are nuclease-resistant.

The oligonucleotides may have a homogenous backbone (e.g., entirely phosphodiester or entirely phosphorothioate) or a heterogeneous (or chimeric) backbone. Phosphorothioate backbone modifications render an oligonucleotide less susceptible to nucleases and thus more stable (as compared to a native phosphodiester backbone nucleic acid) under certain conditions. Other linkages that may provide more stability to an oligonucleotide include without limitation phosphorodithioate linkages, methylphosphonate linkages, methylphosphorothioate linkages, boranophosphonate linkages, peptide linkages, alkyl linkages, dephospho type linkages, and the like. Thus, in some instances, the oligonucleotides have non-naturally occurring backbones.

Oligonucleotides may be synthesized in vitro. Methods for synthesizing nucleic acids, including automated nucleic acid synthesis, are also known in the art. Oligonucleotides having modified backbones, such as backbones comprising phosphorothioate linkages, and including those comprising chimeric modified backbones may be synthesized using automated techniques employing either phosphoramidate or H-phosphonate chemistries. (F. E. Eckstein, "Oligonucleotides and Analogues—A Practical Approach" IRL Press, Oxford, UK, 1991, and M. D. Matteucci and M. H. Caruthers, *Tetrahedron Lett.* 21, 719 (1980)) Aryl- and alkyl-phosphonate linkages can be made, e.g., as described in U.S. Pat. No. 4,469,863; and alkylphosphotriester linkages (in which the charged oxygen moiety is alkylated), e.g., as described in U.S. Pat. No. 5,023,243 and European Patent No. 092,574, can be prepared by automated solid phase synthesis using commercially available reagents. Methods for making other DNA backbone modifications and substitutions have been described. Uhlmann E et al. (1990) Chem Rev 90:544; Goodchild J (1990) Bioconjugate Chem 1:165; Crooke S T et al. (1996) Annu Rev Pharmacol Toxicol 36:107-129; and Hunziker J et al. (1995) Mod Synth Methods 7:331-417.

The oligonucleotides may additionally or alternatively comprise modifications in their sugars. For example, a β-ribose unit or a β-D-2'-deoxyribose unit can be replaced by a modified sugar unit, wherein the modified sugar unit is for example selected from β-D-ribose, α-D-2'-deoxyribose, L-2'-deoxyribose, 2'-F-2'-deoxyribose, arabinose, 2'-F-arabinose, 2'-O—($C_1$-$C_6$)alkyl-ribose, preferably 2'-O—($C_1$-$C_6$) alkyl-ribose is 2'-O-methylribose, 2'-O—($C_2$-$C_6$)alkenyl-ribose, 2'-[O—($C_1$-$C_6$)alkyl-O—($C_1$-$C_6$)alkyl]-ribose, 2'-$NH_2$-2'-deoxyribose, 13-D-xylo-furanose, a-arabinofuranose, 2,4-dideoxy-3-D-erythro-hexo-pyranose, and carbocyclic (described, for example, in Froehler J (1992) Am Chem Soc 114:8320) and/or open-chain sugar analogs (described, for example, in Vandendriessche et al. (1993) Tetrahedron 49:7223) and/or bicyclosugar analogs (described, for example, in Tarkov M et al. (1993) Helv Chim Acta 76:481).

The oligonucleotides may comprise modifications in their bases. Modified bases include modified cytosines (such as 5-substituted cytosines (e.g., 5-methyl-cytosine, 5-fluoro-cytosine, 5-chloro-cytosine, 5-bromo-cytosine, 5-iodo-cytosine, 5-hydroxy-cytosine, 5-hydroxymethyl-cytosine, 5-difluoromethyl-cytosine, and unsubstituted or substituted 5-alkynyl-cytosine), 6-substituted cytosines, N4-substituted cytosines (e.g., N4-ethyl-cytosine), 5-aza-cytosine, 2-mercapto-cytosine, isocytosine, pseudo-isocytosine, cytosine analogs with condensed ring systems (e.g., N,N'-propylene cytosine or phenoxazine), and uracil and its derivatives (e.g., 5-fluoro-uracil, 5-bromo-uracil, 5-bromovinyl-uracil, 4-thio-uracil, 5-hydroxy-uracil, 5-propynyl-uracil), modified guanines such as 7-deazaguanine, 7-deaza-7-substituted guanine (such as 7-deaza-7-(C2-C6)alkynylguanine), 7-deaza-8-substituted guanine, hypoxanthine, N2-substituted guanines (e.g. N2-methyl-guanine), 5-amino-3-methyl-3H,6H-thiazolo[4,5-d]pyrimidine-2,7-dione, 2,6-di-aminopurine, 2-aminopurine, purine, indole, adenine, substituted adenines (e.g. N6-methyl-adenine, 8-oxo-adenine) 8-substituted guanine (e.g. 8-hydroxyguanine and 8-bromoguanine), and 6-thioguanine. The nucleic acids may comprise universal bases (e.g. 3-nitropyrrole, P-base, 4-methyl-indole, 5-nitro-indole, and K-base) and/or aromatic ring systems (e.g. fluorobenzene, difluorobenzene, benzimidazole or dichloro-benzimidazole, 1-methyl-1H-[1,2,4]triazole-3-carboxylic acid amide). A particular base pair that may be incorporated into the oligonucleotides of the invention is a dZ and dP non-standard nucleobase pair reported by Yang et al. NAR, 2006, 34(21):6095-6101. dZ, the pyrimidine analog, is 6-amino-5-nitro-3-(1'-β-D-2'-deoxyribofuranosyl)-2(1H)-pyridone, and its Watson-Crick complement dP, the purine analog, is 2-amino-8-(1'-β-D-1'-deoxyribofuranosyl)-imidazo[1,2-a]-1,3,5-triazin-4(8H)-one.

Methods of Synthesis:

The invention contemplates synthesizing SST motifs through annealing processes. In one approach, once the single stranded oligonucleotides have been identified and synthesized (e.g., using commercial vendors such as Bioneer), they are combined, in a single vessel such as but not limited to a tube, a well, a vial, and the like. The molar amounts of oligonucleotides that are used will depend on the frequency of each oligonucleotide in the motifs desired and the amount of motifs desired. In some embodiments, the oligonucleotides may be present in equimolar concentrations. In some embodiments, each oligonucleotide may be present at a concentration of about 100 nM. The oligonucleotides are placed in a solution. Preferably the solution is buffered although the annealing reaction can also occur in the absence of buffer. The solution may further comprise divalent cations such as but not limited to $Mg^{2+}$. The cation or salt concentration may vary. An exemplary concentration is about 25 mM. The solution may also comprise EDTA or other nuclease inhibitors in order to prevent degradation of the oligonucleotides.

The annealing reaction is carried out by heating the solution and then allowing the solution to slowly cool down. The temperature of the reaction should be sufficiently high to melt any undesirable secondary motif such as hairpin motifs and to ensure that the oligonucleotide species are not bound incorrectly to other non-complementary oligonucleotides. The temperature may therefore be initially raised to about 100° C., about 95° C., about 90° C., about 85° C., 80° C., 75° C., 70° C., 65° C. or 60° C., in some embodiments. The temperature may be raised by placing the vessel in a hot water bath or a heating block or a device capable of temperature control such as a PCR machine. The vessel may be kept in that environment for seconds or minutes. Typically, an incubation of about 1-10 minutes is sufficient.

Once the incubation at elevated temperature is complete, the temperature may be dropped in a number of ways. The temperature may be dropped in an automated manner using a computer algorithm that drops the temperature by a certain amount and maintains that temperature for a certain period of time before dropping the temperature again. Such automated methods may involve dropping the temperature by a degree in each step or by a number of degrees at each step. The vessel may thus be heated and cooled in the same device.

An exemplary process is provided. To effect a drop in temperature from about 90° C. to about 25° C., the temperature is changed from 90° C. to 61° C. in one degree increments at a rate of 10 minutes per degree (i.e., 90° C. for 10 minutes, 89° C. for 10 minutes, etc.). The temperature is then changed from 60° C. to 25° C. in one degree increments and at a rate of about 20 minutes per degree (i.e., 60° C. for 20 minutes, 59° C. for 20 minutes, etc.). The total annealing time for this process is about 17 hours. In accordance with the invention, under these conditions, the oligonucleotides self-assemble into a SST motif of predetermined and desired shape and size.

Alternatively, the vessel may be placed in a different environment, including for example a room temperature environment (e.g., about 25° C.). It is maintained there for an extended period of time in order to allow the oligonucleotides to anneal to each other in the predetermined manner. The cooling down period may last for hours, including without limitation 10, 11, 12, 13, 14, 15, 16, 17, 18, 19 or 20 or more hours. In some instances, the cooling down period is longer than 20 hours and may be 25, 30, 25, 40, 50, 55, 60 or more hours.

The Examples describe a specific annealing process using 100 nM oligonucleotides in a Tris-EDTA (TE), 25 mM $MgCl_2$ solution and heating the solution to about 90° C. and then cooling the solution to about 25° C. over a period of about 17 hours, as described above with a 10 minute per degree drop between 90° C. and 61° C. and a 10 minute per degree drop between 60° C. and 25° C.

Still another set of conditions for self-annealing includes a TE/$Mg^{2+}$ buffer (20 mM Tris, pH 7.6, 2 mM EDTA, 12.5 mM $MgCl_2$) and an identical temperature reduction process.

The stoichiometry of oligonucleotides does not have to be tightly regulated.

Following the annealing process, the reaction mixture may be used directly or it may be further fractionated in order to further isolate the SST motif products. As an example, the reaction mixture may be subjected to gel electrophoresis, such as 2% native agarose gel electrophoresis, in order to physically separate the motif of interest from other motifs or substrates. Typically, a single dominant band is observed. The band may be extracted from the gel and further purified, for example, via centrifugation. The purified product may then be again subjected to gel electrophoresis, with a single band again expected. The purified product may be imaged via AFM or TEM. Such imaging reveals the dimensions of the purified product, the degree and location of any modification (e.g., streptavidin modification), and can be used to determine yield and degree of purity. Such analyses have revealed the formation of motifs having approximately expected dimensions.

Yield of desired product may also be determined post-annealing. "Assembly yield" may be first estimated by native gel electrophoresis, in which the samples are stained with SYBR safe. The yield (referred to as "gel yield") is calculated as the ratio between the fluorescent intensity of the desired product band and that of the entire lane (after background correction). The ratio will therefore be an indicator of the yield. Measured gel yields range from 6-40%. It has been found according to the invention that such ratios may be overestimates since there is apparent motif and sequence-dependent variation in the staining efficiency of SYBR safe. In some instances, the yields may be about 60-100% of the measured gel yield.

The efficiency of the annealing process may also be determined by measuring the fraction of "well-formed" SST motifs as a percentage of all identifiable shapes in an AFM field. The motif is considered to be "well-formed" if it has no defects in its expected outline greater than 15 nm in diameter and no defects in its interior greater than 10 nm in diameter. Following the above criteria, "well-formed" ratios, or "AFM yields" ranging from about 20-85% have been observed across a spectrum of motifs. In certain instances, this ratio is likely an underestimate of the actual ratio of "well-formed" motifs within the purified product, due to the relative fragility of the motif in some instances and the significant post-purification damage that likely occurs during sample deposition or imaging. Such fragility may be mitigated by introducing more covalent bonds into the assembled motifs, e.g. via ligation of two ends of a 4-oligonucleotide SST or crosslinking of neighboring 4-oligonucleotide SSTs.

For some motifs having depth (e.g., tubes or barrels), the degree of well-formed motifs may be determined using TEM imaging. In those instances, the TEM yield was defined as the percentage of identifiable motifs (e.g., tubes or barrels) that measure within 5 nm deviation from the expected full length (e.g., tube or barrel length), based on a 3.5 nm per helical turn estimation.

The invention contemplates manual or automatic means for synthesizing the motifs of the invention. An example of an automatic means, a computer program (e.g., a MATLAB program) provides a graphical interface that displays the canvas from which a motif will be made (e.g., in the case of the 310-oligonucleotide pool, a rectangular canvas is the starting point). Onto that canvas is mapped the desired motif, and the pixels (or SSTs) necessary to synthesize that motif are identified. The program can also help to automate the process of strand picking and mixing using a liquid handling robot (Bravo, Agilent). Thus, once the end user maps the motif to the graphical interface, the computer program outputs instructions for a robotic liquid handler to pick and mix the suitable strands for subsequent annealing. The strand mixture is then used in standard one-pot annealing to produce the shape for AFM imaging. In various tests, each robot batch has been found to produce 48 shapes in roughly 48 hours, effectively reducing several human-hours of labor to 1 machine-hour per shape, and avoids potential human mistakes. Such a robotic system was used to generate 44 of the shapes described herein.

The program interface features three functions: (1) shape design, (2) pipette sequence generation, and (3) protocol output. Using the program, three steps are involved in designing a target shape and generating the preannealing strand mixture for the shape. First, the program displays a schematic of the 2D lattice (the "molecular canvas") and allows the user to either draw a shape from scratch, or upload an image and convert it to a target shape. Then, a list of the constituent strands is generated for the shape. Based on the source strand arrangement in the 96 well plates used by the robot, this strand list is subsequently converted to a list of pipette sequences. Finally, a set of instructions (a runset) are generated in xml format and can be directly loaded and executed by the robot controlling software (VWorks, Agilent).

Composite Motifs:

The invention further contemplates that the SST motifs described herein themselves may be used essentially as monomers or building blocks in order to form higher order or composite motifs. The composite motifs of the invention are comprised of SST motifs linked to each other using linkers. The linkers are typically not integral to the SST motifs although they may be attached to the motifs via suitable functional groups. The ability to attach two or more SST motifs together allows motifs of greater size and complexity to be made.

Figure 2:
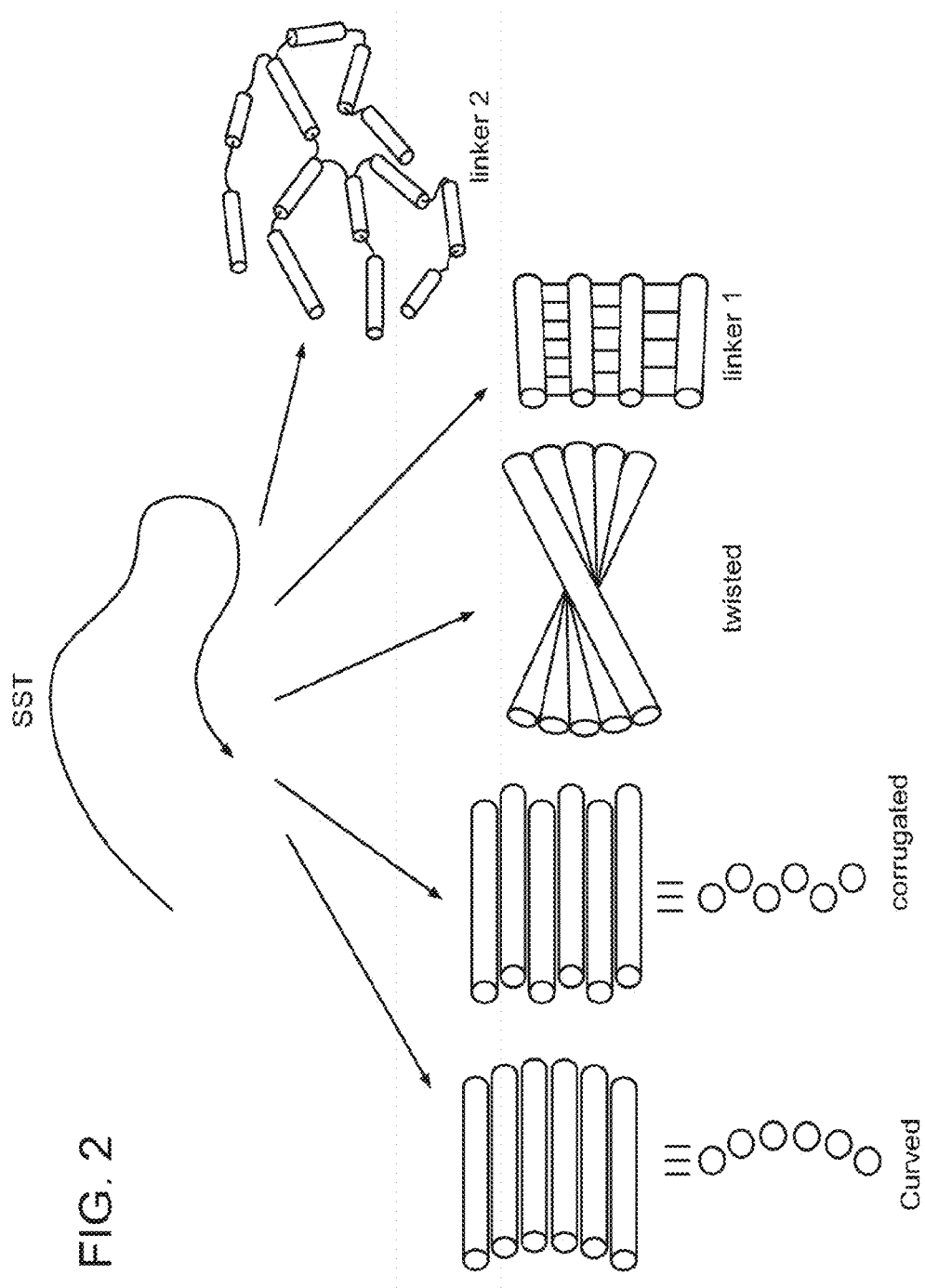
FIG. 2 shows schematics of SST motifs with various geometric properties.
Figure 3:
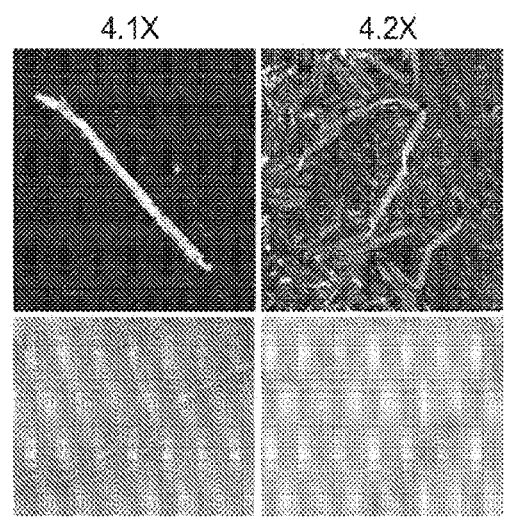
FIG. 3 shows AFM and transmission electron microscopy (TEM) images of curvature characteristics of motifs from different motifs.

The linkers can be added to the ends of SST motifs or to internal loci of the SST motifs to form composite motifs (FIG. 2, compare linker 1 and linker 2).

The dimensions of these composite motifs may range from 500 nm to 100 microns, or 1-1000 microns, without limitation.

Applications:

The SST motifs of the invention may be used in a variety of applications, including those that would benefit from the ability to precisely position and importantly arrange one or more moieties at a nanometer or micron scale.

As an example, the motifs can be used as templates for arranging or patterning inorganic materials such as those useful in electronics, plasmonics, and quantum computing applications. Moieties that may be attached to the SST motifs include metallic particles such as gold nanoparticles (refs. 5, 35), quantum dots (ref. 6), carbon nanotubes (ref. 7), and the like. In this way, the SST motifs provided by the invention act as scaffolds upon which other moieties may be arranged and/or other motifs may be synthesized with nanometer precision and control. For example, carbon nanotubes can be organized into functional molecular electronics systems; tunable geometric arrangement of gold nanoparticles can be used to make functional molecular electronics circuits and novel plasmonics circuits; organized, predetermined arrangement of magnetic particles can be used to make nano-inductors or memory devices; and organized and predetermined arrangement of quantum dots can be used to make novel quantum computers.

In other aspects, the invention contemplates that the SST motifs of the invention may be metalized to make components for electronics. DNA tubes have been metalized into nanowires (refs. 4,15,19). Controlled metallization of the SST motifs of the invention can be used to make, among other things, nano-wires with controlled diameters and hence controlled electronic properties. Further, novel molecular electronic components and circuits can be made through controlled metallization of the strut based SST motifs provided by the invention.

The SST motifs can also be used as templates for biological or organic molecules. Such templated molecules and systems may be useful, for example, in diagnostic and research applications. The biological or organic molecules include without limitation proteins and peptides such as antibodies and antibody fragments, enzymes and enzyme domains, receptors and receptor domains, biological ligands such as hormones and other signaling moieties, polysaccharides, cells, cell aggregates, and the like. Diverse strategies have been demonstrated for templating proteins on DNA lattices (refs. 4, 23, 36). Organization of proteins into prescribed geometric patterns with programmable nanometer precision can be used, for example, to study the cooperative behavior of biological motor proteins (ref. 37). Certain SST motifs may also be used in cell or tissue culture. In these embodiments, as an example, the motifs may be functionalized with biological moieties such as growth factors and extracellular matrix components. In this way, the functionalized motifs may be arranged in culture to mimic a two or three dimensional in vivo environment. As a further example, it is contemplated that higher order functionalize motifs may be made that exhibit a concentration gradient for any particular biological moiety. These systems can then be used to study cellular development, differentiation and/or motion for any number of cell types. In still other instances, higher order motifs of the invention can be used as scaffolds for cellular growth and differentiation in vitro or in vivo.

In various of these applications, the invention further contemplates that the nucleic acid scaffold comprised of the motifs of the invention may be retained or it may be removed (e.g., through digestion or degradation) once it ceased being a template. For example, if the goal is to create a predetermined arrangement of gold particles and such particles are connect to each other as desired independently of the nucleic acid scaffold, the scaffold may be removed, leaving only the gold nanoparticle network.

The following Examples are included for purposes of illustration and are not intended to limit the scope of the invention.

EXAMPLES

Example 1

Methods

DNA Sequence Design.

DNA sequences were designed and optimized using the Uniquimer software to minimize sequence symmetry. For sequence minimization based design, there were several criteria for sequence generation. 1) Nucleotides (i.e. A, C, G, T) were randomly generated one-by-one. 2) Complementary nucleotides to those generated were matched following the base pairing rule: A to T and vice versa, C to G and vice versa. 3) No repeating segment beyond a certain length (8 nt or 9 nt) was permitted. When such repeating segments emerge during design, the most recently generated nucleotides were mutated until the repeating segment requirement was satisfied. 4) No four consecutive A, C, G or T bases were allowed. 5) Pre-specified nucleotides at the single stranded linkage points were used to avoid sliding bases around the linkage points. For designs using completely random sequences, restrictions in steps 3 to 5 were not applied. Manual design and/or optimization was introduced for linker sequence design (e.g., linkers between some (motifs XIV.1-XIV.4) or all (motif XIV.5) domains).

Sample Preparation.

Single stranded oligonucleotides were synthesized by Integrated DNA Technology, Inc. or Bioneer Corperation. To assemble the SST motifs, oligonucleotides were mixed stoichiometrically to a final concentration of 100 nM in 0.5×TE/Mg$^{++}$ buffer (20 mM Tris, pH 7.6, 2 mM EDTA, 12.5 mM MgCl$_2$) (for some motifs, oligonucleotides were mixed stoichiometrically to a final concentration of 200 nM) based on 24×28 rectangular lattice and annealed in a PCR thermo cycler by cooling from 90° C. to 25° C. over a period of 17 to 58 hours with different cooling programs. The annealed samples were then applied to a ý ý ñ 다 예 汇Aᴛ 다 외 stained with SYBR® safe) in a bath of ice water. Then the target gel bands were excised and placed into a Freeze 'N Squeeze spin column (Bio-Rad Laboratories). The gel pieces were crushed into fine pieces using a microtube pestle in the column, and the column was then directly applied for centrifugation at 2000 rpm for 3 minutes. Samples brought through the column were collected, and the sample concentration was estimated by ultraviolet (UV) absorption at 260 nm. Alternatively, the excised gel band was placed in a 1.5 mL Eppendorf tube and crushed with a microtube pestle. A 2× to 3× gel piece volume of 0.5×TE/Mg$^{++}$ was then added to the tube to elute the DNA motif out of the gel (4° C. overnight). Then the purified DNA motif in elution buffer was collected after a brief centrifugation, and its concentration was estimated by the measurement of UV absorption at 260 nm. Streptavidin labeling was done with two different approaches, as follows.

(1) Labeling the Poly-T End of Tube Motifs.

After tube purification, 3' biotin-modified poly-A strands (5-10 folds in molar ratio to the poly-T counterparts) were mixed with the sample at room temperature overnight. The sample was then imaged by atomic force microscopy (AFM). After the first round of imaging, streptavidin (1 L of 10 mg/mL in 0.5×TE/Mg$^{++}$ buffer) was added to the imaging sample on mica for an incubation of 2 minutes prior to imaging again.

(2) Labeling the Top and Bottom Row or Internal Loci of 24H×28T Rectangle.

Each oligonucleotide of the top and bottom rows (or internal loci) of a 24×28 rectangular was modified to have a 3' 17-nucleotide (nt) handle (TT as spacer and GGAAGGGATGGAGGA (SEQ ID NO:1) to be complementary to the 3' biotin-modified strand with a sequence of TCCTCCATCCCTTCC-biotin (SEQ ID NO:2)). The remaining component oligonucleotides of the rectangular lattice were mixed with 3' biotin-modified strands (1-2 fold to the linkers), which were complementary to the linker sequence of the oligonucleotides of the top and bottom rows, in TE/Mg$^{++}$ buffer for annealing, and then the agarose gel was purified. The purified sample was then imaged by AFM. After the first round of imaging, streptavidin (1 µL of 10 mg/mL in 0.5×TE/Mg$^{++}$ buffer) was added to the imaging sample for an incubation of 2 minutes, and then the sample was imaged again.

Robot Automation for Sample Preparation.

A custom MATLAB program was used to aid the design of complex motif shapes and to automate single stranded oligonucleotide mixing by a liquid handling robot (Bravo, Agilent). For each motif shape, 5 µL of 10 µM of each single stranded oligonucleotide was chosen and mixed into a final volume of 2 mL and then vacuum evaporated to a 250 nM, 200 µL final mixture, ready for annealing. Each run accommodated 48 shapes and took two days to complete.

Atomic force microscopy (AFM) imaging. AFM images were obtained using an SPM Multimode with Digital Instruments Nanoscope V controller (Vecco). A 5 µL drop (2 to 5 nM) of annealed, purified sample with a 40 µL drop of 1×TE/Mg$^{++}$ was applied onto the surface of a freshly cleaved mica and left for approximately 2 minutes. Sometimes, additional dilution of the sample was performed to achieve the desired sample density. On a few occasions, supplemental 10 mM NiCl$_2$ was added to increase the strength of DNA-mica binding. The AFM tips were short and thin cantilever in a SNL-10 silicon nitride cantilever chip (Vecco Probes).

Transmission Electron Microscopy (TEM) Imaging.

For imaging, 3.5 µL sample (1-5 nM) were adsorbed onto glow discharged carbon-coated TEM grids for 4 minutes and then stained using a 2% aqueous uranyl formate solution containing 25 mM NaOH for 1 minute. Imaging was performed using an JEOL JEM-1400 operated at 80 kV.

Yield Quantification by Fluorescent Labeling.

Yield was first estimated by agarose gel electrophoresis analysis. The ratio between the fluorescence intensity of target band and that of the entire lane was adopted to present the gross yield of structural formation. This simple calculation from component strands of imperfect stoichiometry may not have been a high fidelity representation of formation yield. Therefore, a more careful study from limiting component strands with fluorescent labeling was carried out. Two oligonucleotides of the 24H×28T rectangle were modified with Cy3 and Alexa 647, respectively. They were mixed with the remaining oligonucleotides for the lattice in 0.5 fold (e.g., when the concentration of the other individual oligonucleotides was around 200 nM, the concentration of the fluorescent strands was set to be 100 nM) in 0.5TE/$Mg^{++}$ buffer for annealing. The annealed sample was applied to an 2% agarose gel without SYBR® safe pre-stain (there was cross-talk between the SYBR® safe channel and Cy3 channel). The gel was then scanned with a typhoon gel scanner using specific fluorescent channels (e.g., Cy3 and Alexa 647). After scanning, the gel was stained with SYBR® safe and then scanned again to make sure the Cy3/Alexa647 band was the target band, by superimposing the SYBR® safe band with the Cy3/Alexa 647 channel.

Measurement and Statistics.

AFM measurement was done using Nanoscope Analysis (version 1.20) provided by Veeco. The cross section function was applied for the distance measurement task (lengths and widths of the rectangles of different sizes). Near perfect motifs were chosen for the measurements. TEM images of the tubes were analyzed using ImageJ (version 1.43u) by NIH. Straight Line function was applied to measure the width of a specific tube. Segmented Line function was applied to highlight and measure the contour length of a specific tube. Thirty sample points were collected for each distance measurement (e.g., width of 24H×28T lattice) and the statics (e.g., average, standard deviation) were based on the thirty data points.

Results

The SST motifs provided herein were designed to self-assemble with a size of around 10 helical by 11 helical turns (10H×11T). Most motifs contained 66 distinct SST species (e.g., 45 internal, full-length SSTs, 9 full-length SST on vertical boundaries whose exposed single stranded domains are replaced by poly-T, 10 half-length SSTs on horizontal boundaries, including 2 half-length SSTs with poly-T replaced single stranded domains at corners). The SST motifs were made using un-purified DNA strands with randomly designed sequences and were mixed without careful adjustment of stoichiometry. After single-step ("one-pot") annealing from 90° C. to 25° C. for 17 h in 0.5×TE buffer with 15 mM $Mg^{++}$, the solution was subjected to 2% native agarose gel electrophoresis, which produced one dominant band.

Annealed samples were subjected to atomic force microscopy (AFM) imaging and showed the expected rectangular or parallelogram morphology with approximately the expected dimensions. For samples with relatively low yields, motifs were purified from bands of the 2% agarose gel; purified samples were subjected to AFM imaging. AFM image quality was improved after gel-based purification.

Curvature.

Figure 4:
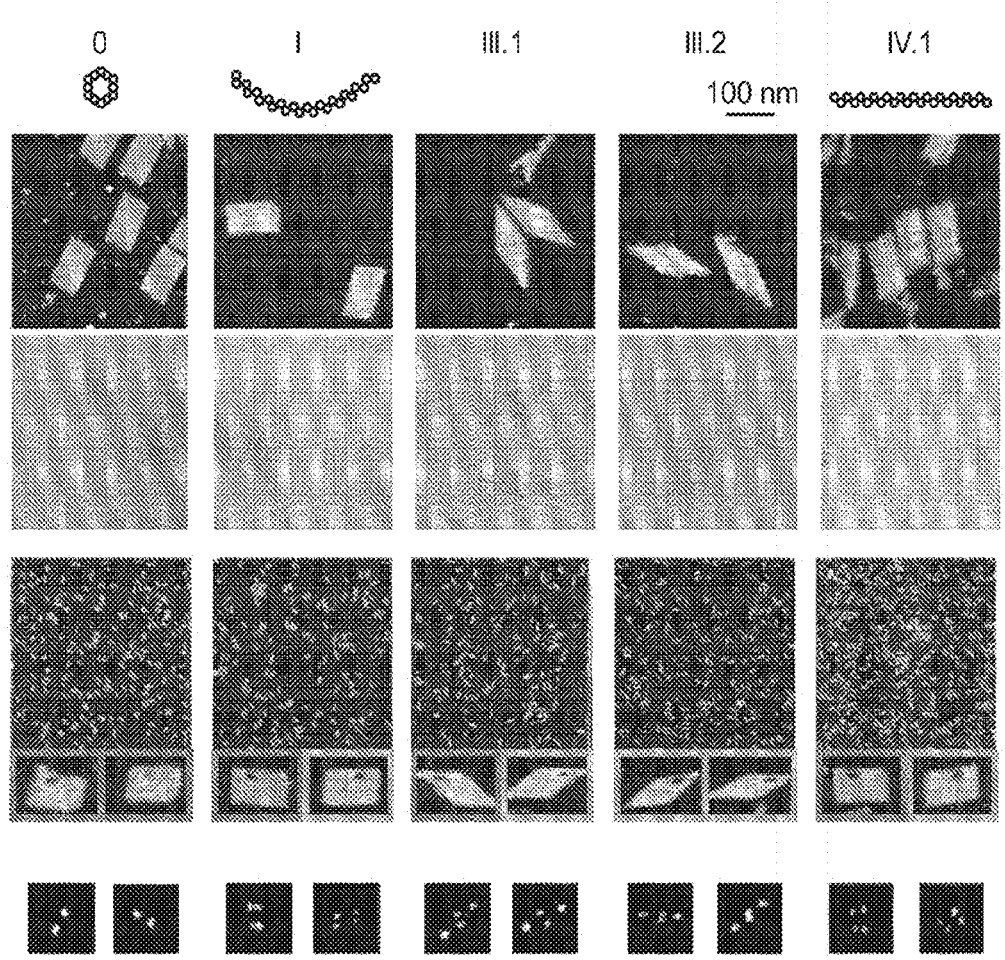
FIG. 4 shows AFM and TEM images of curvature characteristics from different SST motifs.

Large SST motifs (e.g., 24H×29T) were designed for the curvature study. Sequence design and self-assembly were conducted in a fashion similar to their 10H×11T counterparts. The annealed samples were subjected to 2% native gel electrophoresis, then the desired band was extracted and purified by centrifugation. The purified samples were later characterized. As shown by AFM imaging, regardless of designed curvature, lattice motifs were shaped as flat, single layer motifs on the mica surface. By contrast, the lattice motifs appeared more "realistic" when imaged by transmission electron microscopy (TEM). A dense roll was observed for the rolled up rectangle motif 0 (720° curvature expected); a reduced curvature was observed in the rectangle motif 6 (88° curvature expected); and a more flat rectangle (perfectly corrugated) was observed for motif 1. A flat and a rolled up parallelogram were observed for motifs 9 and 10, respectively. The different curvature conformations of the motifs were confirmed by two other assays. The first assay was the AFM-based landing assay (FIG. 4). A small hole was introduced to the top-left corners of five different motifs as an orientational marker. If such a marker showed up at the top left corner more often than its mirror image (top right corner), this was an indication that the motif curved up rather than down. By contrast, if the mirror image showed up more often than not, this was an indication that the motif curved down rather than up. If the marker shows no bias landing on either side, the motif was presumed to be flat. The experimental results showed perfectly biased landing for the extremely rolled up motifs in a presumed curving direction. However, because of limited sampling space, the assay did not differentiate between slightly curved motifs and perfectly flat motifs. The other methodology for curvature characterization was a super resolution imaging-based assay.

Curvature of the SST motifs was a major focus of this study. Curvature can be adjusted by complementary domain length arrangement. However, there will always be a major groove/minor groove phase shift, so the curvature will not be perfectly canceled out, especially when only one species of SST is used for a single motif. The most flat motif obtained out of a single species of U-shaped oligonucleotide is 4° per helix (e.g., as shown in motif 1). There is also a way to arrange a kink in between curved helices, but they are not as elegant as the corrugated design. The major groove/minor groove shift is canceled out producing a the Z-shaped motif, which produced a corrugated design. When the crossover points were defined to be collinear with the centers of the adjacent helices, the curvature of calculation was not consistent with the experiment. If the crossover points were designed to be offset to the collinear positions by degree alpha, the curvature calculation could be fit to consistency with the experimental results (e.g., as shown in motif 3.1 and 3.2). When the design was changed to motif 4.1, which is a symmetric design, the offset of angle alpha was canceled out as well to make this design a perfect corrugation design. Later experiments showed that the perfectly corrugated design produced a slightly curved motif. The non-perfectly flat motifs were observed under TEM and super-resolution imaging. In particular, the extension study indicated that the corrugated motif is curved because the extension along the parallel direction could lead to tube formation of different circumferences. There is a certain amount of flexibility along the parallel direction of the single layer motif and adjacent helices can fluctuate from perfectly flat configuration to a slightly curved configuration. The constant motion is in equilibrium but transient configuration can be recorded under TEM or super-resolution microscopy, hence some curved motifs showed up. In a similar regime, the extended motifs of different width curved along the parallel direction so that the top and bottom rows of the motif met transiently and resulted in the zipping through of the entire row to form tubes of different circumferences.

Twist.

The "twist" of different motifs was studied in extension experiments. The extension studies were applied to motif 4.1 and 4.2. Instead of designing poly-T boundary oligonucleotides for the vertical boundaries of the rectangle, the boundary oligonucleotide were designed so that the leftmost column of the oligonucleotides paired with the rightmost column of the rectangle. Because the motif was rather rigid along the helical axis, it was not cyclized by itself. Rather, multiple units of rectangles aligned in tandem to form long polymers with individual rectangles as monomer units. Because of the long stretch of the polymers, the twist became more visible under AFM or TEM. The polymer long stretch obtained from motif 4.1 was straight, indicating the 10.5 base pairs per turn did not lead to an obvious twist. On the other hand, the polymer stretch from motif 4.2 was spiral, suggesting zero to 10.5 base pairs per turn (e.g., 10 base pairs per turn) leads to a twist.

Flexibility.

Motifs 14.x have linkers of different lengths in between two groups of complementary domains. The resulting motifs showed an increased spacing in between helices. When single stranded linker domains were paired with complementary strands (e.g., motif 14.3), a grid-like morphology was shown, rather than parallel. Results also showed valid SST motif formation using linkers introduced to every two adjacent complementary domains. The linkers in motif 14.5 broke the continuous double helices, so the resulting motif became amorphous under AFM imaging. However, once the complementary strand to the linker region was added in, it took a more ordered shape under AFM. The conformational change upon addition of the complementary strands to the linker regions indicated that the motif designed with SST-linker type is dynamic.

Surprisingly, motifs 14.1-14.5 showed that motifs with linkers of different lengths can lead to the formation of ordered motifs. This was surprising because, it was thought in the field was that the stacking of helices is one of the reasons why the DNA nanostructures can form. Motif XIV.5 represents an extreme example in which there are linkers in between every adjacent complementary domain. In the resulting motif, individual double-stranded domains, which are 10/11 base pairs long, were connected by single stranded linkers. There were no long duplex DNA to hold the motif in place, so the motif was loosely entangled without precise morphology. To make sure the motif self-assembled as expected, poly-A (multiple adenine bases) strands were added, after annealing, to be complementary to the poly-T counterparts, thereby forcing the motif to take a more ordered morphology. After such treatment, a grid-like SST motif was observed, which confirmed that the motif self-assembled in a desired fashion. In addition to the 10H×11T size, another motif formed a 24H×29T lattice, indicating that the linker motif is also as scalable as the other SST motifs.

REFERENCES

Each of the references below is incorporated herein in its entirety.

1. Seeman, N. Nature 2003, 421, 427-431.
2. Feldkamp, U.; Niemeyer, C. Angewandte Chemie International Edition 2006, 45, 1856-1876.
3. Bath, J.; Turberfield, A. Nature Nanotechnology 2007, 2, 275-284.
4. Yan, H.; Park, S. H.; Finkelstein, G.; Reif, J. H.; LaBean, T. H. Science 2003, 301(5641), 1882-1884.
5. Le, J. D.; Pinto, Y.; Seeman, N. C.; Musier-Forsyth, K.; Taton, T. A.; Kiehl, R. A. Nano Lett. 2004, 4, 2343-2347.
6. Sharma, J.; Ke, Y.; Lin, C.; Chhabra, R.; Wang, Q.; Nangreave, J.; Liu, Y.; Yan, H. Angew. Chem. Int. Ed. 2008, 47, 5157-5159.
7. Chen, Y.; Liu, H. P.; Ye, T.; Kim, J.; Mao, C. D. J. Am. Chem. Soc. 2007, 129.
8. Douglas, S. M.; Chou, J. J.; Shih, W. M. Proc. Natl Acad. Sci. USA 2007, 104, 6644-6648.
9. Fu, T. J.; Seeman, N. C. Biochemistry 1993, 32, 3211-3220.
10. Winfree, E.; Liu, F.; Wenzler, L.; Seeman, N. Nature 1998, 394, 539-544.
11. Rothemund, P. Nature 2006, 440, 297-302.
12. Douglas, S.; Dietz, H.; Liedl, T.; Högberg, B.; Graf, F.; Shih, W. Nature 2009, 459, 414-418.
13. Dietz, H.; Douglas, S.; Shih, W. Science 2009, 325, 725-730.
14. Mitchell, J. C.; Harris, J. R.; Malo, J.; Bath, J.; Turberfield, A. J. J. Am. Chem. Soc. 2004, 126, 16342-16343.
15. Liu, D.; Park, S.; Reif, J.; LaBean, T. Proceedings of the National Academy of Sciences of the U.S. Pat. No. 2,004,101, 717-722.
16. Rothemund, P. W. K.; Ekani-Nkodo, A.; Papadakis, N.; Kumar, A.; Fygenson, D. K.; Winfree, E. J. Am. Chem. Soc. 2004, 126, 16344-16353.
17. Rothemund, P.; Papadakis, N.; Winfree, E. PLoS Biology 2004, 2, 2041-2053.
18. Mathieu, F.; Liao, S.; Kopatscht, J.; Wang, T.; Mao, C.; Seeman, N. C. Nano Lett. 2005, 5, 661-665.
19. Park, S. H.; Barish, R.; Li, H. Y.; Reif, J. H.; Finkelstein, G.; Yan, H.; LaBean, T. H. Nano Lett. 2005, 5, 693-696.
20. Liu, H.; Chen, Y.; He, Y.; Ribbe, A.; Mao, C. Angew. Chem. Int. Ed. 2006, 45, 1942-1945.
21. Kuzuya, A.; Wang, R. S.; Sha, R. J.; Seeman, N. C. Nano Lett. 2007, 7, 1757-1763.
22. Schulman, R.; Winfree, E. Proc. Natl Acad. Sci. USA (in press) 2007, 104, 15236-15241.
23. Lin, C.; Yan, L.; Rinker, S.; Yan, H. ChemBioChem (in press) 2006.
24. Yin, P.; Hariadi, R.; Sahu, S.; Choi, H. M. T.; Park, S. H.; LaBean, T. H.; J. H. Reif, Science 2008, 321, 824-826.
25. Yin, P.; Choi, H. M. T.; Calvert, C. R.; Pierce, N. A. Nature 2008, 451, 318-322.
26. Yurke, B.; Turberfield, A.; Mills, Jr., A.; Simmel, F.; Neumann, J. Nature 2000, 406, 605-608.
27. Pieles, U.; Englisch, U. Nucleic Acids Research 1989, 17, 285-299.
28. Killops, K.; Campus, L.; Hawker, C. Journal of the American Chemical Society 2008, 130, 5062-5064.
29. Winfree, E. On the computational power of DNA annealing and ligation. In DNA Based Computers; Lipton, R.; Baum, E., Eds.; American Mathematical Society: Providence, R.I., 1996.
30. Winfree, E. Algorithmic Self-Assembly of DNA, Ph.D. thesis thesis, California Institute of Technology, 1998.
31. Rothemund, P. W. K.; Winfree, E. The program-size complexity of self-assembled squares (extended abstract). In Proceedings of the thirty-second annual ACM symposium on Theory of computing; ACM Press: 2000.
32. Barish, R. D.; Schulman, R.; Rothemund, P. W. K.; Winfree, E. Proceedings of the National Academy of Sciences 2009, 106, 6054.

33. Chen, H. L.; Cheng, Q.; Goel, A.; Huang, M. D.; Espanes, P. M. d. Invadable self-assembly: Combining robustness with efficiency. In Proceedings of the 15th annual ACM-SIAM Symposium on Discrete Algorithms (SODA); 2004.
35. Sharma, J.; Chhabra, R.; Cheng, A.; Brownell, J.; Liu, Y.; Yan, H. Science 2009, 112-116.
36. Li, H.; LaBean, T. H.; Kenan, D. J. Organic and Biomolecular Chemistry 2006, 3420-3426.
38. Yin, P.; Yan, H.; Daniell, X.; Turberfield, A. J.; Reif, J. Angewandte Chemie International Edition 2004, 43, 4906-4911.
39. Yin, P.; Turberfield, A. J.; Reif, J. H. Designs of Autonomous Unidirectional Walking DNA Devices. In Proc. 10th International Meeting on DNA Computing; 2004.
40. Reif, J. H.; Sahu, S.; Yin, P. Compact Error-Resilient Computational DNA Tiling Assemblies. In Proc. 10th International Meeting on DNA Computing; 2004.
41. Reif, J. H.; Sahu, S.; Yin, P. Complexity of Graph Self-assembly in Accretive Systems and Self-Destructible Systems. In Proc. 11th International Meeting on DNA Computing; 2005.
42. Sahu, S.; Yin, P.; Reif, J. H. A Self-Assembly Model of Time-Dependent Glue Strength. In Proc. $11^{th}$ International Meeting on DNA Computing; 2005.
43. Park, S. H.; Yin, P.; Liu, Y.; Reif, J. H.; LaBean, T. H.; Yan, H. Nano Letters 2005, 5, 729-733.
44. Yin, P.; Hartemink, A. J. Bioinformatics 2005, 21, 869-879.
45. Sekulic, A.; Hudson, C. C.; Homme, J. L.; Yin, P.; Otterness, D. M.; Karnitz, L. M.; Abraham, R. T. Cancer Research 2000, 60, 3504-3513.
46. PCT/US12/49306

EQUIVALENTS

While several inventive embodiments have been described and illustrated herein, those of ordinary skill in the art will readily envision a variety of other means and/or motifs for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A nucleic acid structure comprising
a plurality of annealed motifs, wherein each of the motifs comprises four oligonucleotides, each of the oligonucleotides comprises at least four domains arranged into at least two parallel double helices, every domain of an oligonucleotide of the plurality is bound to a domain of another oligonucleotide of the plurality to form a plurality of S-shaped oligonucleotides, and the nucleic acid structure is curved, corrugated or twisted.

2. The nucleic acid structure of claim 1, wherein each oligonucleotide comprises at least six domains.

3. The nucleic acid structure of claim 1, wherein the length of each domain of a single oligonucleotide is the same.

4. The nucleic acid structure of claim 1, wherein the length of at least two domains, at least three domains or at least four domains of a single oligonucleotide is the same.

5. The nucleic acid structure of claim 1, wherein the length of each domain of a single oligonucleotide is different.

6. The nucleic acid structure of claim 1, wherein the oligonucleotides are 18-104 nucleotides in length.

7. The nucleic acid structure of claim 1, wherein the length of the domains of the oligonucleotides range from 4 nucleotides to 13 nucleotides.

8. The nucleic acid structure of claim 1, wherein the nucleic acid structure is comprised of different types of oligonucleotides.

9. The nucleic acid structure of claim 1, further comprising a linker between at least two domains.

10. The nucleic acid structure of claim 1, wherein the single stranded oligonucleotides are DNA oligonucleotides.

11. The nucleic acid structure of claim 1, wherein the single stranded oligonucleotides are L-DNA oligonucleotides.

12. The nucleic acid structure of claim 1, wherein the nucleic acid structure further comprises double crossovers.

13. A composition comprising a plurality of nucleic acid structures of claim 1, wherein the plurality is at least 50% homogeneous.

14. A method of producing the nucleic acid structure of claim 1, the method comprising
annealing a plurality of single stranded oligonucleotides in a single vessel to form the nucleic acid structure, wherein at least one single stranded oligonucleotide is present at a molar concentration that is at least 10-fold lower than the molar concentration of other oligonucleotides in the plurality.

15. The method of claim 14, wherein a first subset of oligonucleotides comprises 2 domains and a second subset of oligonucleotides comprises 4 domains or 6 domains.

16. A composite nucleic acid structure comprising at least two nucleic acid structures of claim 1, conjugated to each other through a linker.

17. The nucleic acid structure of claim 1, wherein one or more of the oligonucleotide(s) is conjugated to a moiety selected from the group consisting of a metallic, organic, or inorganic moiety.

18. The nucleic acid structure of claim 17, wherein the moiety is a metallic moiety selected from gold nanoparticles, quantum dots, and carbon nanotubes.

19. The nucleic acid structure of claim 1, wherein one or more of the oligonucleotide(s) is conjugated to a nucleic acid moiety.

20. The nucleic acid structure of claim 19, wherein the nucleic acid moiety binds to one or more oligonucleotide(s) in the nucleic acid structure.

21. The nucleic acid structure of claim 19, wherein the nucleic acid moiety comprises a triplex forming oligonucleotide.

22. The nucleic acid structure of claim 19, wherein the nucleic acid moiety comprises a region of complementarity to the one or more oligonucleotide(s) in the nucleic acid structure.

23. The nucleic acid structure of claim 1, wherein one or more of the oligonucleotide(s) is conjugated to a non-nucleic acid moiety.

24. The nucleic acid structure of claim 23, wherein the non-nucleic acid moiety is attached covalently or non-covalently to the oligonucleotides.

25. The nucleic acid structure of claim 23, wherein the non-nucleic acid moiety is a protein, peptide, or polysaccharide.

26. The nucleic acid structure of claim 23, wherein the non-nucleic acid moiety is a growth factor or an extracellular matrix component.

* * * * *

SEQUENCE LISTING

```
<160> NUMBER OF SEQ ID NOS: 2

<210> SEQ ID NO 1
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 1
ggaagggatg gagga                                                          15

<210> SEQ ID NO 2
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 2
tcctccatcc cttcc                                                          15
```